(12) United States Patent
Soliman et al.

(10) Patent No.: US 11,864,739 B2
(45) Date of Patent: Jan. 9, 2024

(54) SURGICAL RETRACTOR

(71) Applicants: John Selim Soliman, Crystal Beach, FL (US); Matthew L. Bycer, Phoenix, AZ (US)

(72) Inventors: John Selim Soliman, Crystal Beach, FL (US); Nagi Bolos Kalad, Holiday, FL (US)

( * ) Notice: Subject to any disclaimer, the term of this patent is extended or adjusted under 35 U.S.C. 154(b) by 0 days.

(21) Appl. No.: 17/737,912

(22) Filed: May 5, 2022

(65) Prior Publication Data

US 2022/0257232 A1 Aug. 18, 2022

Related U.S. Application Data

(63) Continuation-in-part of application No. PCT/US2020/059222, filed on Nov. 5, 2020.

(51) Int. Cl.
*A61B 1/32* (2006.01)
*A61B 17/02* (2006.01)
*A61B 17/00* (2006.01)

(52) U.S. Cl.
CPC ............ *A61B 1/32* (2013.01); *A61B 17/0206* (2013.01); *A61B 17/0293* (2013.01); *A61B 2017/00407* (2013.01); *A61B 2017/00473* (2013.01); *A61B 2017/0256* (2013.01)

(58) Field of Classification Search
CPC .................. A61B 1/32; A61B 17/0206; A61B 2017/0256; A61B 17/0293; A61B 17/3439; A61M 29/00
See application file for complete search history.

(56) References Cited

U.S. PATENT DOCUMENTS

| 1,428,653 | A | * | 9/1922 | Nick | A61M 29/02 |
| | | | | | 606/41 |
| 2,083,573 | A | * | 6/1937 | Clifford, V | A61B 1/32 |
| | | | | | 606/198 |
| 4,130,113 | A | * | 12/1978 | Graham | A61B 17/0293 |
| | | | | | 600/224 |
| 6,312,443 | B1 | * | 11/2001 | Stone | A61F 2/4455 |
| | | | | | 623/1.1 |
| 6,855,149 | B2 | | 2/2005 | Dye | |
| 7,344,495 | B2 | * | 3/2008 | Ravikumar | A61B 17/3423 |
| | | | | | 600/233 |
| 7,435,219 | B2 | | 10/2008 | Kim | |
| 8,550,995 | B2 | | 10/2013 | Frasier et al. | |
| 8,727,975 | B1 | | 5/2014 | Pfabe et al. | |

(Continued)

*Primary Examiner* — Larry E Waggle, Jr.
(74) *Attorney, Agent, or Firm* — Bycer & Marion, PLC; Matthew L. Bycer; Michael B. Marion

(57) ABSTRACT

An apparatus and methods for a spinal retractor utilizing spirally retracting blades to provide a surgical portal. The retractor system comprises a blade assembly and mechanism to open and close the blades. The blade assembly comprises a set of blades arranged in a mostly circular formation coupled to an actuator. The retractor system utilizes a mechanism such as a slot-and-follower to actuate the blades in a spiral motion. Each blade in the blade assembly maintains tangential contact to each adjacent blade during expansion and contraction of the device. The circumferential retractor blade arrangement completely separates the soft tissue being retracted from the surgical portal being created allowing for the surgical site to be free from any encroaching internal tissue.

20 Claims, 26 Drawing Sheets

(56) References Cited

U.S. PATENT DOCUMENTS

| | | |
|---|---|---|
| 9,386,916 B2 | 7/2016 | Predick et al. |
| 9,498,200 B2 | 11/2016 | Pfabe et al. |
| 9,545,250 B2 | 1/2017 | Pfabe et al. |
| 9,693,761 B2 * | 7/2017 | Fedorov .............. A61B 17/0293 |
| 2008/0114209 A1 | 5/2008 | Cohen et al. |
| 2014/0275801 A1 | 9/2014 | Menchaca et al. |
| 2017/0143325 A1 | 5/2017 | Lynn et al. |

* cited by examiner

SURGICAL RETRACTOR

CLAIM OF PRIORITY

The present application includes subject matter disclosed in and claims priority to PCT application entitled "Surgical Retractor" filed Nov. 5, 2020 and assigned Serial No. PCT/US20/059222; and includes subject matter disclosed in provisional application entitled "Spirally Expanding Blade System for Reduced Trauma Surgical Retractor" filed Nov. 5, 2019, and assigned Ser. No. 62/973,982, describing inventions made by the present inventors, herein incorporated by reference.

BACKGROUND OF THE INVENTION

1. Field of the Invention

The present invention relates to surgical devices such as surgical retractor systems. More particularly, the present invention relates to surgical retractor devices for retracting anatomy to provide exposure of an operating site, such as for a spinal procedure.

2. Description of Related Prior Art

Surgical retractor systems are used to obtain and maintain access to the anatomy being operated on during a surgical procedure. For most surgeries, several layers of tissue must be dissected through and moved aside (retracted) in order to access the anatomy to be operated on. It may be necessary to retract soft tissues, such as skin, muscle, fat, and internal organs or bony tissue, or both. While dissecting to reach the surgical site, the surgeon must also avoid damaging certain tissues, such as neural or vascular structures. A retractor system allows the surgical team to access the surgical site by pushing the tissues aside and holding them in place while doing minimal damage to those tissues and protecting particularly sensitive tissues such as nerves or vascular structures. In many cases, one or more hand-held retractors are used to obtain and maintain access to a surgical site. These hand-held retractors are available in a large variety of sizes and shapes, depending on the type of surgery being performed and the type of exposure required.

Surgical retractors can be highly specialized for a particular procedure. For example, specialized retractors were developed for minimally invasive orthopedic joint surgery that allow the surgeon to gain access to the joint being operated on while minimizing the incision size and more importantly, minimizing the damage done to soft tissue while accessing the surgical site. For example, Dye et al. (U.S. Pat. No. 6,855,149 B2) describes a retractor specifically used for preparing the acetabulum and implanting the acetabular component as a part of total hip arthroplasty surgery.

Lumbar spinal surgery, in particular the direct lateral surgical approach, presents a particular set of challenges for surgical access. The distance from skin to the lateral aspect of the lumbar vertebrae can be up to 180 mm and yet the diameter of the access portal should not be greater than 50 mm. After the skin incision, the abdominal musculature is divided until the retroperitoneal space is reached. Blunt dissection is continued until the psoas muscle is reached. The psoas muscle is divided until the intervertebral space can be accessed. Sequential dilation is used to open up a large enough space in the psoas muscle to insert a lateral specific retractor. The abdominal musculature and the psoas muscle must be pushed and held in place by the retractor. The peritoneum must be pushed and held anterior. The portal to access the intervertebral space is opened up to around 50 mm. The goal of the process is to achieve access to the surgical site without injuring any critical anatomy including the great vessels, neural structures, the bowels, and organs within the retroperitoneal space.

Direct lateral spine surgery has several clinical benefits. This surgical approach allows for a large interbody spacer to be utilized, compared to what posterior or transforaminal approaches allow for, allowing for much more stability of the fused joint. Lateral cages can have much larger lordotic angles, which allows for more anatomic lordosis of the spine to be achieved. Anterior interbody cages have these benefits as well, but the anterior approach is much more invasive and a general surgeon would need to access the anterior aspect of the spine before the intervertebral space can be prepared and the device implanted. The direct lateral approach is also a less invasive procedure. The incision size is small and the portal through the abdominal muscles and the psoas muscle is made by splitting the muscle fibers using blunt dissection.

State of the art lateral specific retractors utilize a two, three, or four blade design to achieve retraction of the soft tissues to achieve a surgical portal to the intervertebral space. Lynn et. al. (US 2017/0143325 A1) and Kim et. al. (U.S. Pat. No. 7,435,219 B2) show a four-blade retractor design and Predick et. al. (U.S. Pat. No. 9,386,916 B2) shows a three-blade retractor design. The retractor blades can be opened independently, as with the four-blade retractor, or in some designs two or more blades can be opened simultaneously, as with the three-blade retractor. The blades can also be angled outward to increase the surgical exposure near the intervertebral body space or to compensate for the blades bending inward due to retracting force. The blades are moved apart so that a portal of around 51 mm is opened up, allowing access to the intervertebral space. The retractor is usually rigidly clamped to the frame of the operating table to keep it in place. Fixation pins are also commonly used to attach the blades to the vertebral bodies to maintain position at the surgical site.

The retractors described in the prior art have some problems that require attention. Cost is a major issue for most lateral retractors. In some cases a lateral retractor system can cost as much as USD$80,000 to USD$100,000. Much of this cost is due to the complexity of the retractor designs. They typically consist of many moving parts and each part must be made to tight manufacturing tolerances in order to work correctly. A less complex, cost-effective retractor design would benefit the state of the art of the lateral spine surgery industry.

Another issue with the prior art is that the working portal is not completely separated from the surrounding tissues by the blades of the retractor. The surrounding tissues are not protected completely from the surgical instruments being used to prepare the interbody space. Furthermore, the surrounding soft tissues can actually enter the retractor working portal through the gaps between the blades, greatly increasing the risk of soft tissue injury happening during the surgical procedure. For example, when using a typical three-blade retractor to maintain a working portal to the surgical site, there are three large areas of exposed soft tissue between each of the blades and some soft tissue may even encroach into the working portal.

It is therefore a primary object of the present invention to provide a cost-effective surgical retractor system wherein the surgical site is protected by a surgical portal free from any encroaching tissue.

The present invention has several advantages over state of the art lateral retractors. Embodiments of the invention comprise a circumferential retractor blade arrangement that completely separates the soft tissue being retracted from the surgical portal that is created. This helps prevent injury to surrounding soft tissue from occurring during the procedure. Furthermore, with the soft tissue being retracted circumferentially, the retraction force is being distributed around the entire circumference of the surgical portal resulting in lower retraction pressure. With three- or four-blade retractors, the retraction force is concentrated at only three or four points along the circumference, resulting in higher pressure being applied to the retracted soft tissue. The expanding protector further reduces risk to soft tissue during the retraction process. The invention described herein is also much less complicated, from a manufacturing perspective, than most current lateral spinal surgery retractors. Moreover, another advantage is that the retraction system engages all of the blades at the same time whereas current retractors require mechanisms to drive each blade separately.

These and other objects of the present invention will become apparent to those skilled in the art as the description thereof proceeds.

SUMMARY OF THE INVENTION

The present invention is directed to a multi-blade surgical retractor system that spirally contracts and expands used for lateral lumbar fusion surgery, among other medical uses. The retractor generally comprises a set of blades and the mechanism to open and close the blades. The system preferably uses eight blades, but any number of blades may be used. The retractor blades are arranged in a mostly circular formation, wherein each blade overlaps the next blade. Each blade moves in a mostly spiral motion, while simultaneously rotating as the retractor opens so that each blade slides away from the previous blade while remaining in constant tangential contact. The result is a retractor that opens and closes without any gaps between the blades.

In some embodiments, when the retractor is in the fully closed position (that is, with no surgical portal being provided), the blades may be nested together in the shape of a circle. The curvature of the blades, the number of blades, and the thickness of the blades may be optimized to achieve a minimal closed diameter. Alternatively, the shape of the blades may be optimized to allow for a maximized opened diameter. In some embodiments, the retractor blades may open in 6 mm diameter increments. The retractor blades maintain tangential contact during the entire process of open and closing the device.

Many mechanisms are present in various embodiments of the invention to open and close the surgical portal of the retractor system. One mechanism that can be used to provide the spiral motion and rotation of the blades is a slot-and-follower type of cam mechanism. In a preferred embodiment, two slots and two followers are required to provide both the spiral and rotational motion. Pairs of curved slots are cut into the guide plate. These slots guide a corresponding pair of follower pins which are rigidly coupled to each blade. A second plate has radial slots cut into it. Each of these radial slots guide a third follower pin that is rigidly connected to each blade. The second plate can be rotated coaxially to the first plate. As the second plate is rotated against the first plate, each radial slot in the second plate pushes the third follower pin in each blade along a trajectory guided by the first and second follower pins on each blade moving through the pair of slots in the first plate. As the first and second follower pins attached to the blade are pushed through the two slots in the first plate, the blade is forced to rotate and move away from the axis of the retractor. The blades moving away from the central axis of the retractor causes the working portal to expand and the rotation of the blades causes the blades to be in constant tangential contact so there is no gap between them.

In one realization of the invention, there is a first and second handle on each plate which is used to rotate the second plate relative to the first plate. Rotating the second plate in one direction would cause the retractor to open and rotating the second plate in the other direction would cause the retractor to close.

Another possible realization would use a ratcheting mechanism to hold the retractor in the open position and then be released to allow the retractor to close. The latch can be attached to the first plate and the ratchet teeth cut into the second plate, configured so that as the retractor is opened, the ratcheting mechanism maintains the retractor opened until it is released.

In another possible realization, a worm and gear mechanism can be utilized to drive and hold the rotation of the second plate relative to the first plate. This embodiment may provide for more force to be applied when opening the retractor as a worm and gear mechanism can provide a significant amount of mechanical advantage and will not require a ratchet since worm and gear mechanisms are self-retaining. The worm may be attached to the first plate so that the worm is tangential to the outside of the second plate. The teeth of the gear may be located on the outer diameter of the second plate. To release the retractor without closing it the worm may be disengaged with the teeth of the gear as a part of a release mechanism.

In another realization of the retractor system, the tip of the retractor may be bullet-nosed to allow for easier insertion into the surgical site. When performing minimally invasive lateral lumbar spine surgery, a Kirschner wire (K-wire) is inserted through the soft tissue down to the target surgical site. Dilators of increasing diameter are then inserted over the K-wire until the minimum diameter of the surgical retractor is reached. At this point, the surgical retractor may be inserted over the dilator and then expanded to form a surgical portal. Having a retractor with a bullet-nosed shape provides the advantage of being an easier fit over the last dilator.

The present invention may also include an expanding protector that wraps around the outside of the retractor blades. This protector is generally comprised of a rolled-up piece of thin plastic sheet. The material of the sheet should preferably be flexible and have a low coefficient of friction. Polytetrafluoroethylene (PTFE), known by the brand name Teflon®, is an example of the ideal material for the protector, but ultra-high-molecular-weight-polyethylene (UHMWPE) or any other similar material may be used. The spring tension in the rolled up plastic maintains the diameter of the roll smaller than the diameter of the retractor blades when it is in the free state. As the surgical retractor is expanding, the protector expands to accommodate the expanding diameter of the retractor blades.

The present invention further includes a method for providing access to portions of a patient's internal body by retracting tissues by inserting a distal end of a blade assembly including a plurality of coaxial blades through an incision in the patient's body into a cavity. The blade assembly may then be expanded to define a channel set between the blades. Preferably, at least at some time during the expansion, causing an exterior side of at least one of the blades to contact with an interior edge of an adjacent blade. This may form a surgical portal through the channel. The blade assembly is preferably coupled to a guide plate, wherein each of the blades includes a base coupled, preferably to a blade holder which is then coupled to a pin that is set in a slot of the guide plate. The blade assembly orientation may be locked to retain a fixed diameter of the channel. The locking may be accomplished by a pawl set into a tooth, or teeth, of a top plate, the top plate may be rotatably coupled with the guide plate, a dn the locking fixes the relative orientation of the guide plate to the top plate. The tip of one of the blades may be fixed relative to an internal organ, such as a vertebrae or disc, via a sharp pointed pin or shim. The surgical site may be accessed through a proximal end of the channel, preferably through an aperture set through the top plate and guide plate, the apertures aligned. After surgery, the blade assembly may be contracted to reduce the diameter of the channel. The tool may then be withdrawn from the patient's body. A sleeve may be placed around the blade assembly to prevent contact of blades with internal tissues.

The expansion and contraction of the blade assembly may be accomplished by moving pins coupled with each blade through slots in both the guide plate and top plate. Relative rotation of the plates may be accomplished by worm drive gear, pinion and rack, twisting handles, or otherwise. Pins may move in preset slots in the guide plate, and top plate, the slots in the gtop plate radially extending from a central aperture.

BRIEF DESCRIPTION OF THE DRAWINGS

The present invention will be described with greater specificity and clarity with reference to the following drawings, in which.

DETAILED DESCRIPTION OF THE PREFERRED EMBODIMENTS

Figure 1:
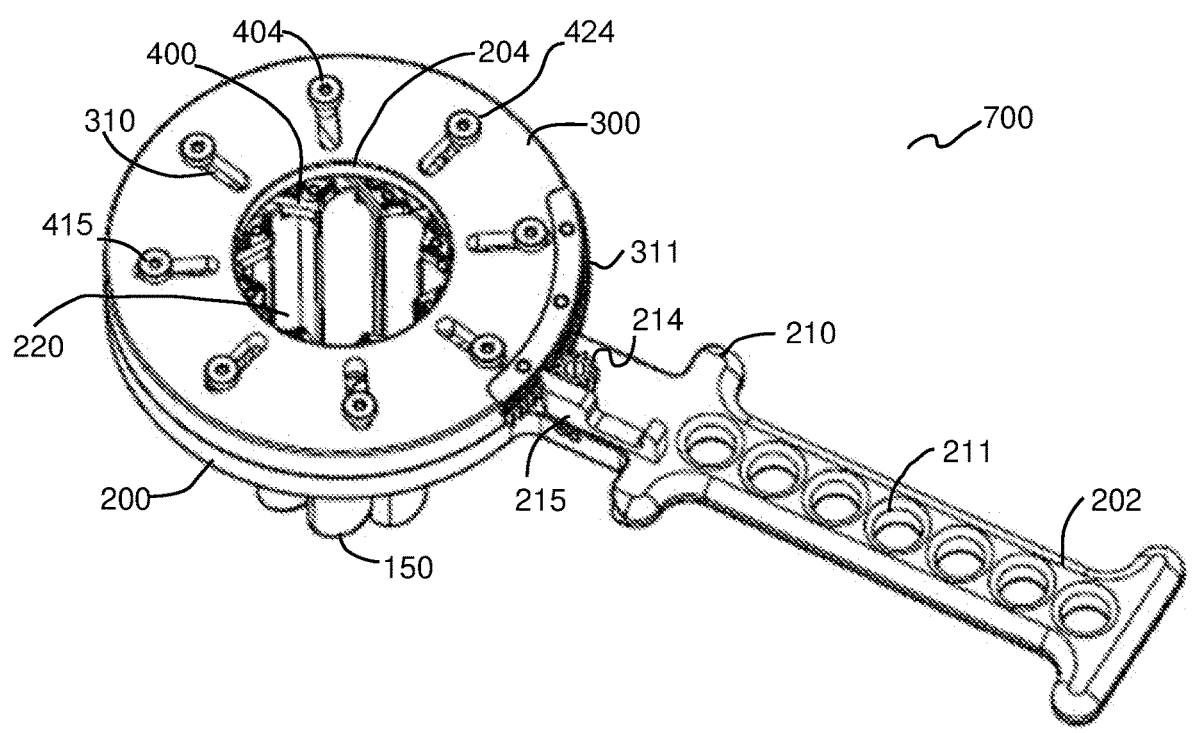
FIG. 1 illustrates a perspective view of the surgical retractor system utilizing a ratcheting mechanism consistent with at least one embodiment of the present disclosure.
Figure 2:
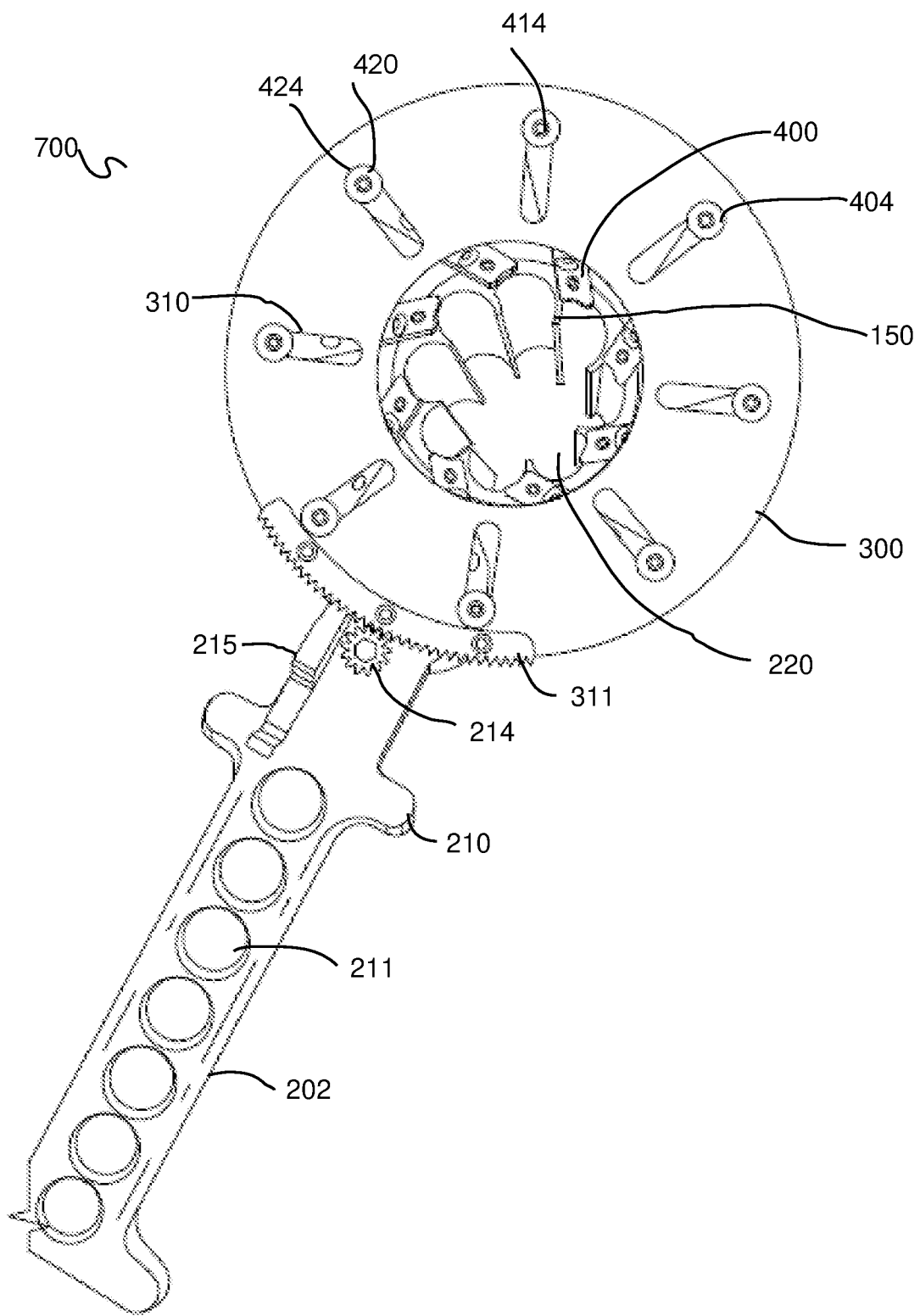
FIG. 2 illustrates a top view of the surgical retractor system utilizing a ratcheting mechanism consistent with at least one embodiment of the present disclosure.
Figure 15:
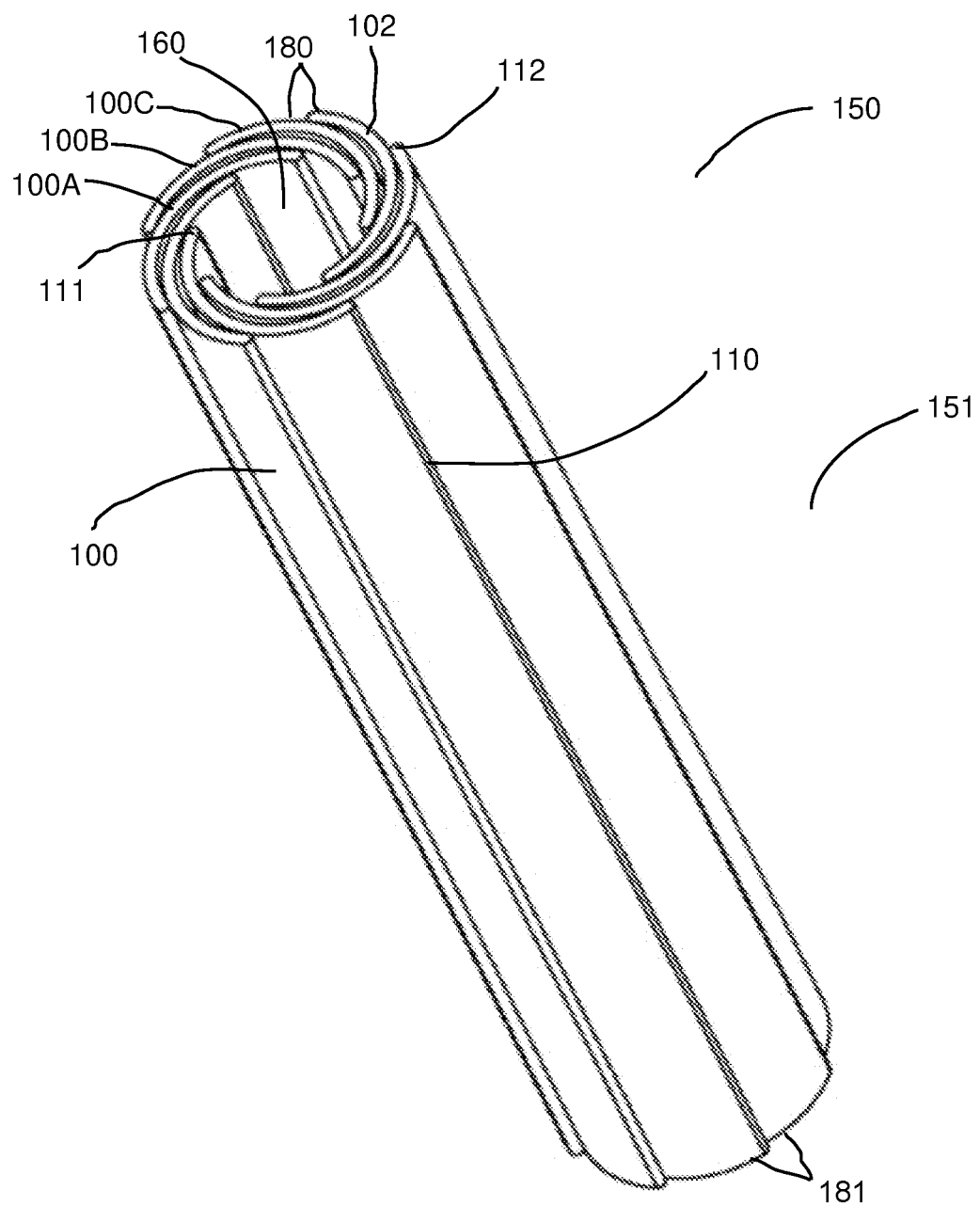
FIG. 15 illustrates a perspective view of the contracted blade assembly consistent with at least one embodiment of the present disclosure.

Referring to FIGS. 1 and 2, a preferred embodiment of surgical retractor system 700 is shown. The system is generally composed of blade assembly 150 made up of a plurality of blades 100, guide plate 200, and optionally including handle 202 either affixed to guide plate 200 or top plate 300, and top plate 300. Blade assembly 150 includes the plurality of blades 100, preferably wherein each blade is aligned co-axially and perpendicular to a plane of the guide plate 200. Each blade preferably has curvature 102 similar to all other blades 100. Blades 100 each define their own longitudinal axis 104, the longitudinal axis 104 of all blades 100 aligning in parallel. The blades 100 are assembled in an overlapping circular formation 110, wherein each blade 100 has interior edge 111 and exterior edge 112 that overlap each adjacent blade 100 as shown in FIG. 15. The interior side 114 of each blade 100 interfaces with the exterior side 116 of its neighbor in circular repetitive format. The blades 100 can contract to form a contracted assembly 151 and expand to form an expanded assembly 152, always defining cylindrical channel 154 of varying diameter.

Figure 16:
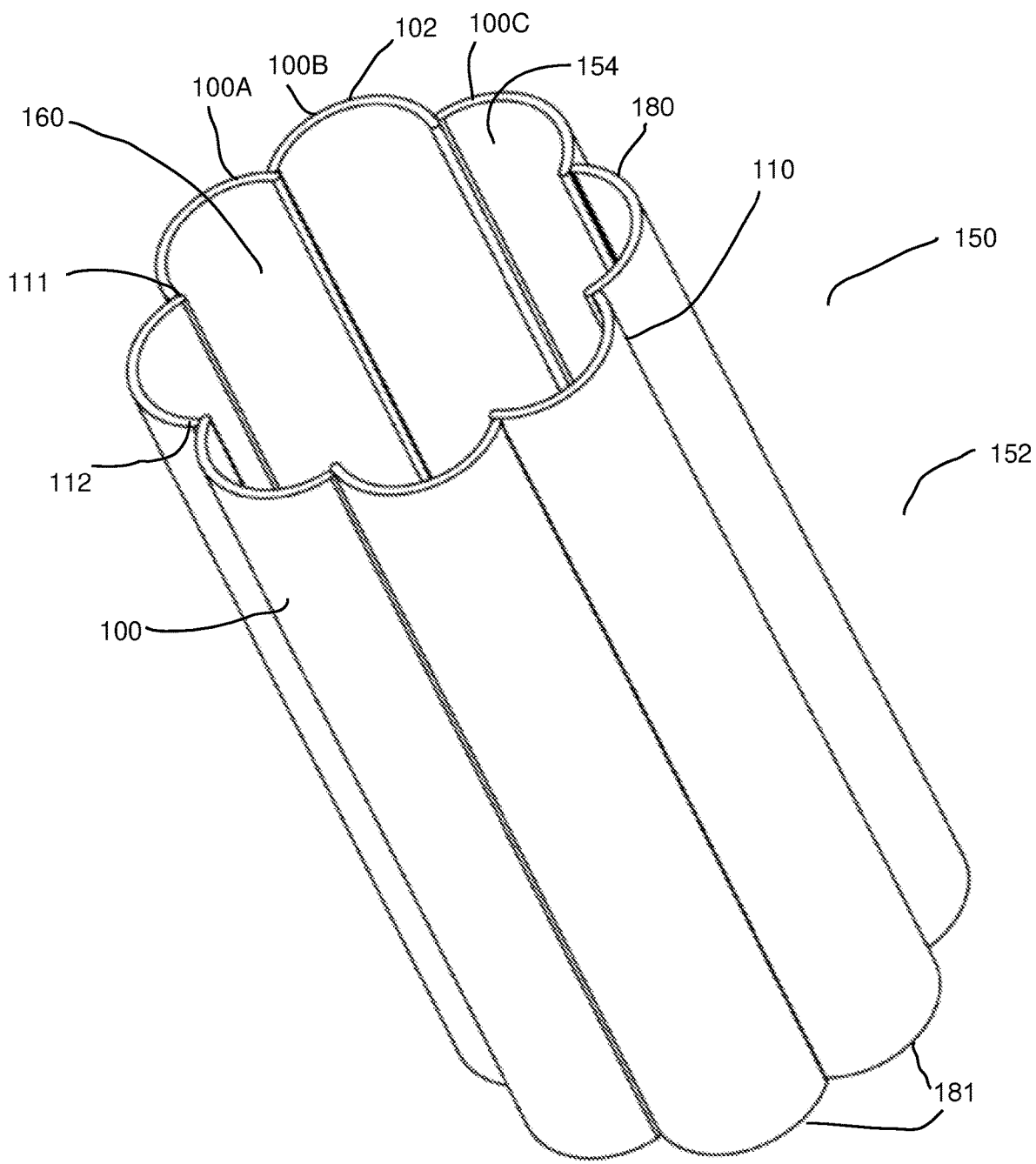
FIG. 16 illustrates a perspective view of the expanded blade assembly consistent with at least one embodiment of the present disclosure.
Figure 17:
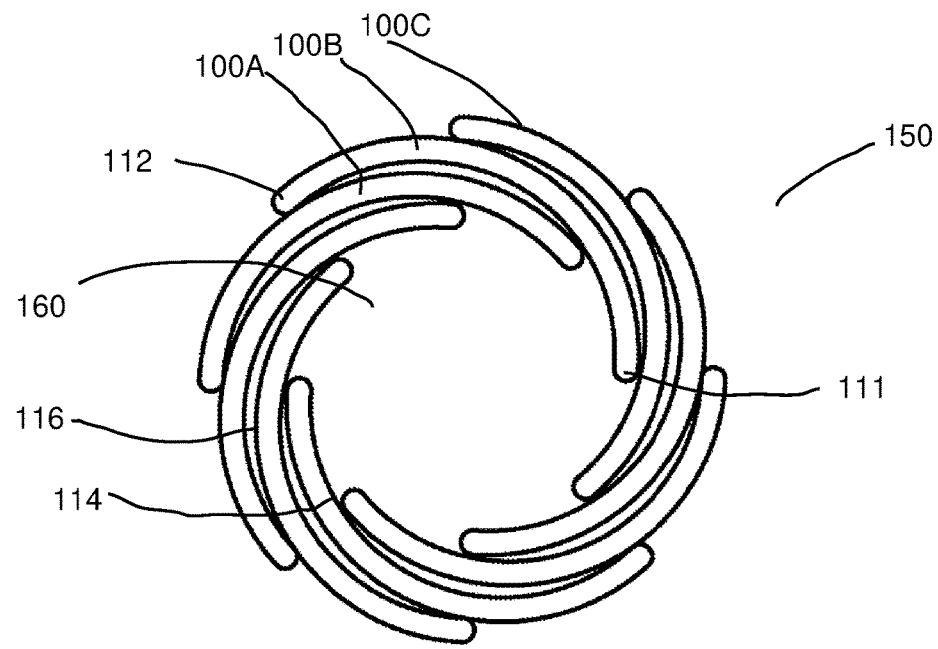
FIG. 17 illustrates a top view of the blade assembly in a contracted state consistent with at least one embodiment of the present disclosure.
Figure 18:
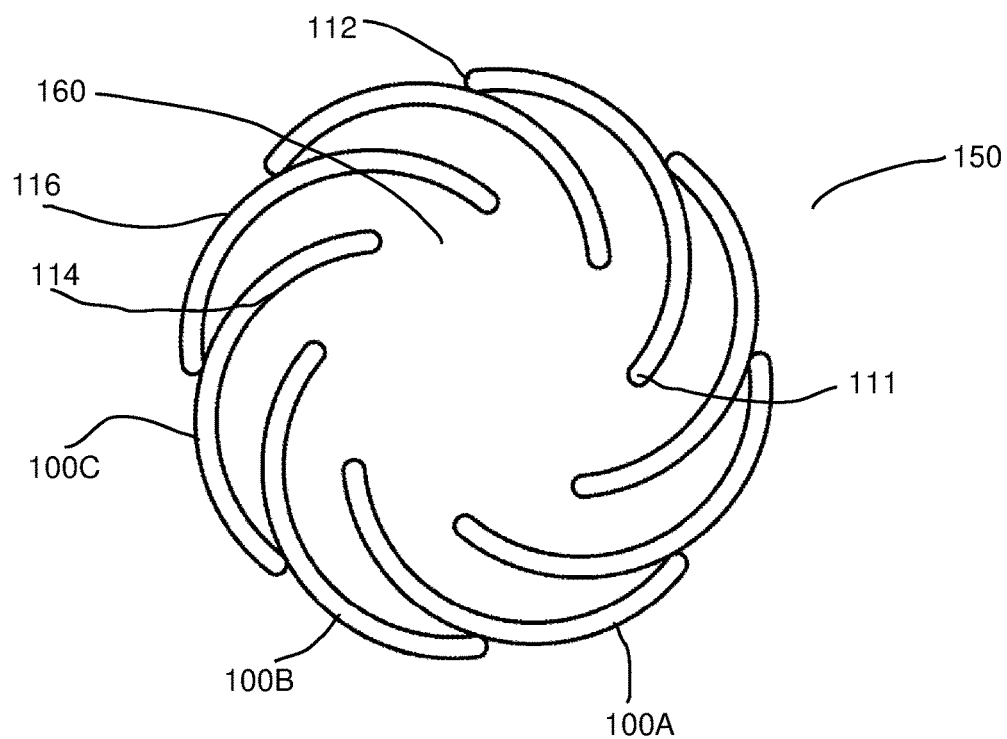
FIG. 18 illustrates another top view of the blade assembly consistent with at least one embodiment of the present disclosure.
Figure 19:
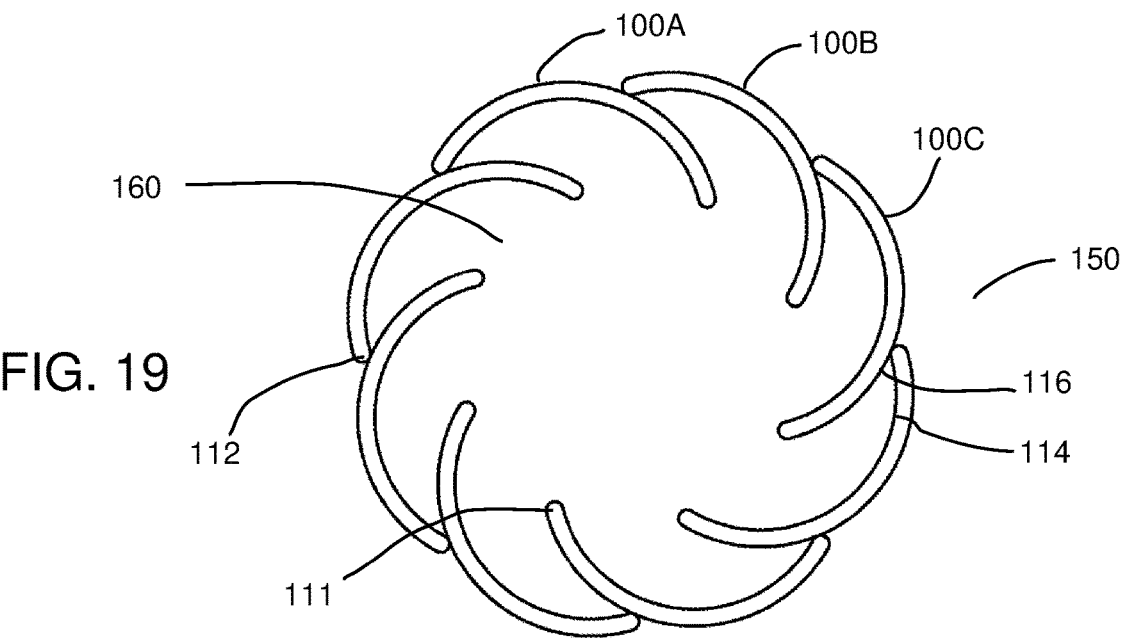
FIG. 19 illustrates another top view of the blade assembly consistent with at least one embodiment of the present disclosure.
Figure 20:
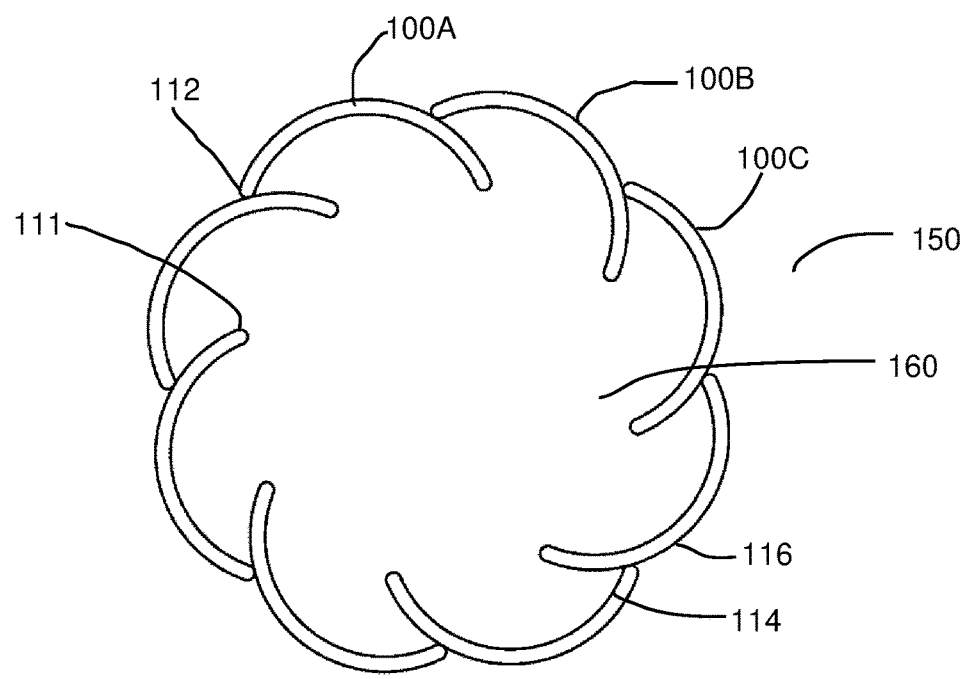
FIG. 20 illustrates another top view of the blade assembly in a slightly more expanded state than FIG. 19 consistent with at least one embodiment of the present disclosure.
Figure 21:
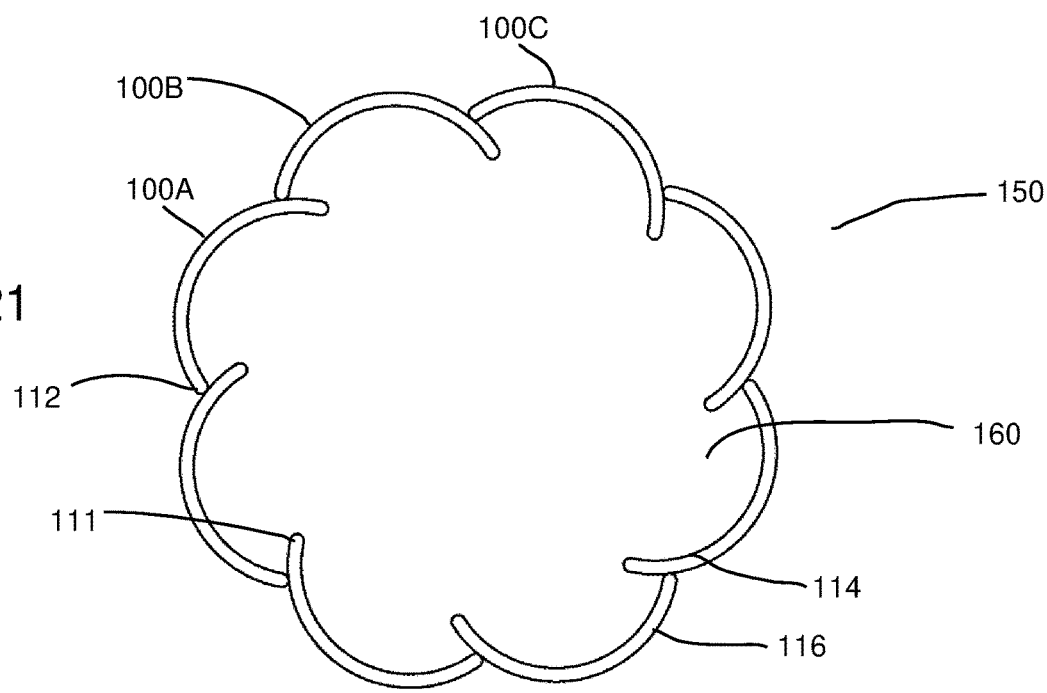
FIG. 21 illustrates another top view of the blade assembly consistent with at least one embodiment of the present disclosure.
Figure 22:
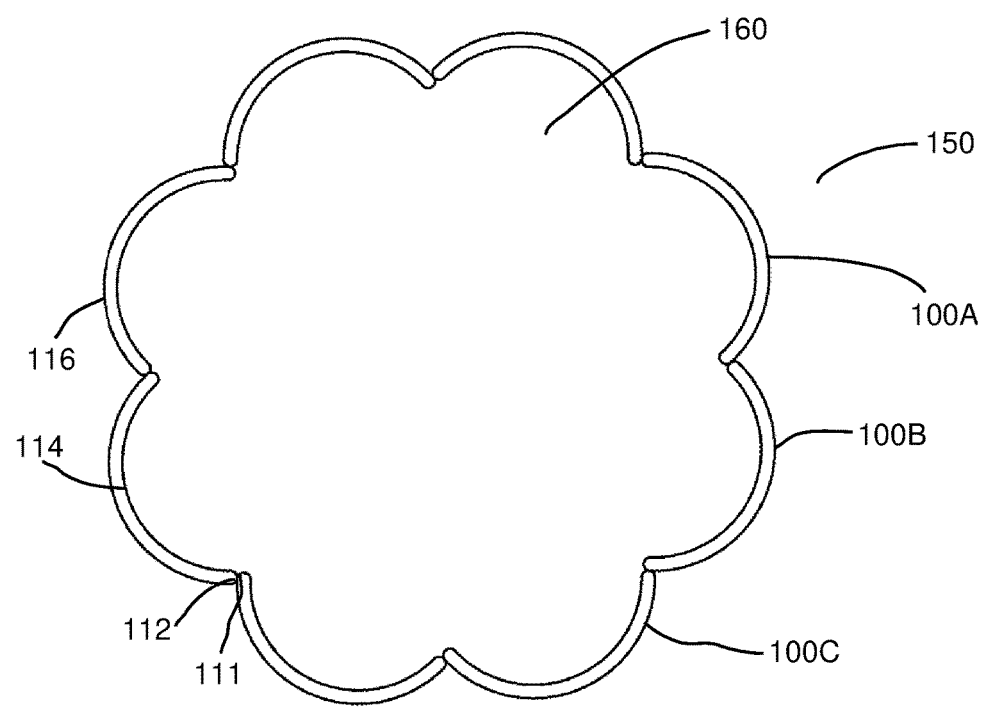
FIG. 22 illustrates another top view of the blade assembly consistent with at least one embodiment of the present disclosure.

Cylindrical channel 154 provides access to an interior (often artificially created) cavity in a body, and acts as surgical portal 160 as shown in FIG. 16. For instance, the surgical portal may be used to access the spine, vertebrae and/or nervous system through the abdomen. For the purposes of this invention, "cylindrical channel" may be defined as any shape formed by the blade assembly 150 which resembles a flower-like cylindrical shape or otherwise during the contracting and expanding phase of blade assembly 150 to form surgical portal 160 as can be seen in FIGS. 17-22. In each of FIGS. 17-22, a preferred number of blades, eight individual blades 100, are shown, but any number of blades may be used. Each blade 100 in blade assembly 150 may include a tip 101 and a base 121. Preferably, blade base 121 of each blade is coupled to guide plate 200 via blade assembly holder 400. Blade assembly holder 400 acts to couple blade 100 to guide plate 200. Blade assembly holder 400 allows each blade to move through tracks 230 into the guide plate 200. Tracks 230 are preferably arranged to cause blades to move and rotate in a spiral-like motion, as the blade assembly holders 400 move through predetermined paths in tracking slots 208 and 209 in guide plate 200. Various embodiments of the guide plate 200 motive types are considered to power or drive opening and closing of blade assembly 150. In some embodiments, guide plate 200 provides a path to move blades 100 using a variety of mechanisms such as a slot-and-follower mechanism, a ratcheting mechanism, a worm-gear mechanism, or any other open-close mechanism. It is preferred that tracking slots 230 cause the expansion and contraction of the blade assembly 150 in a manner to allow the blades 100 to maintain contact or near-contact with each of its two neighboring blades 100 to continue to define an expanding and/or contracting channel 154.

Figure 3:
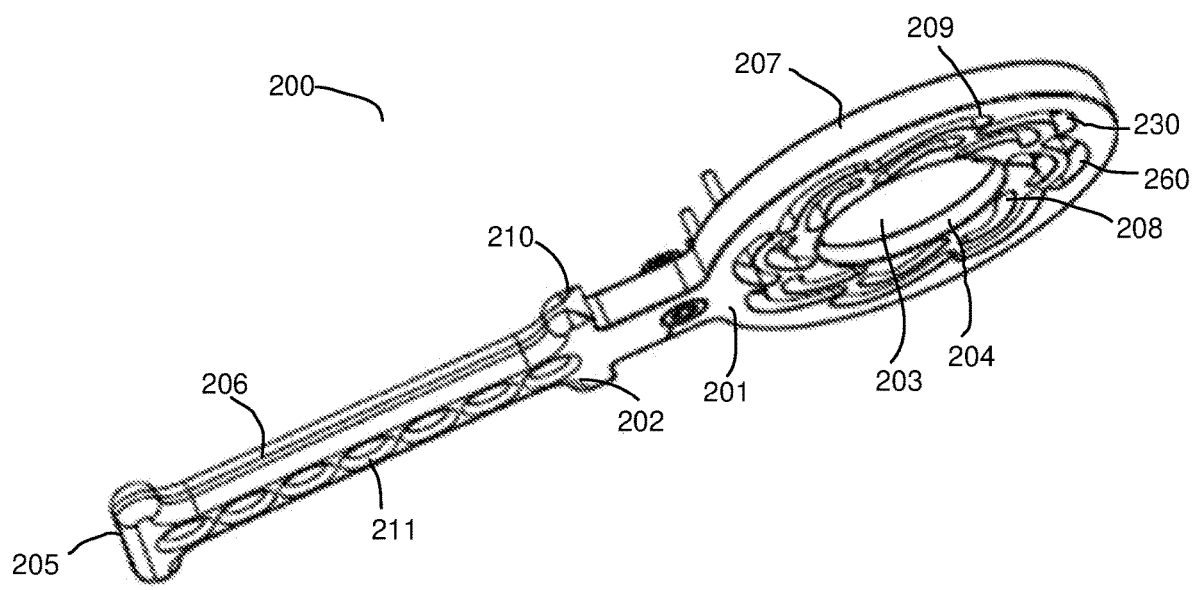
FIG. 3 illustrates a perspective view of the guide plate consistent with at least one embodiment of the present disclosure.
Figure 4:
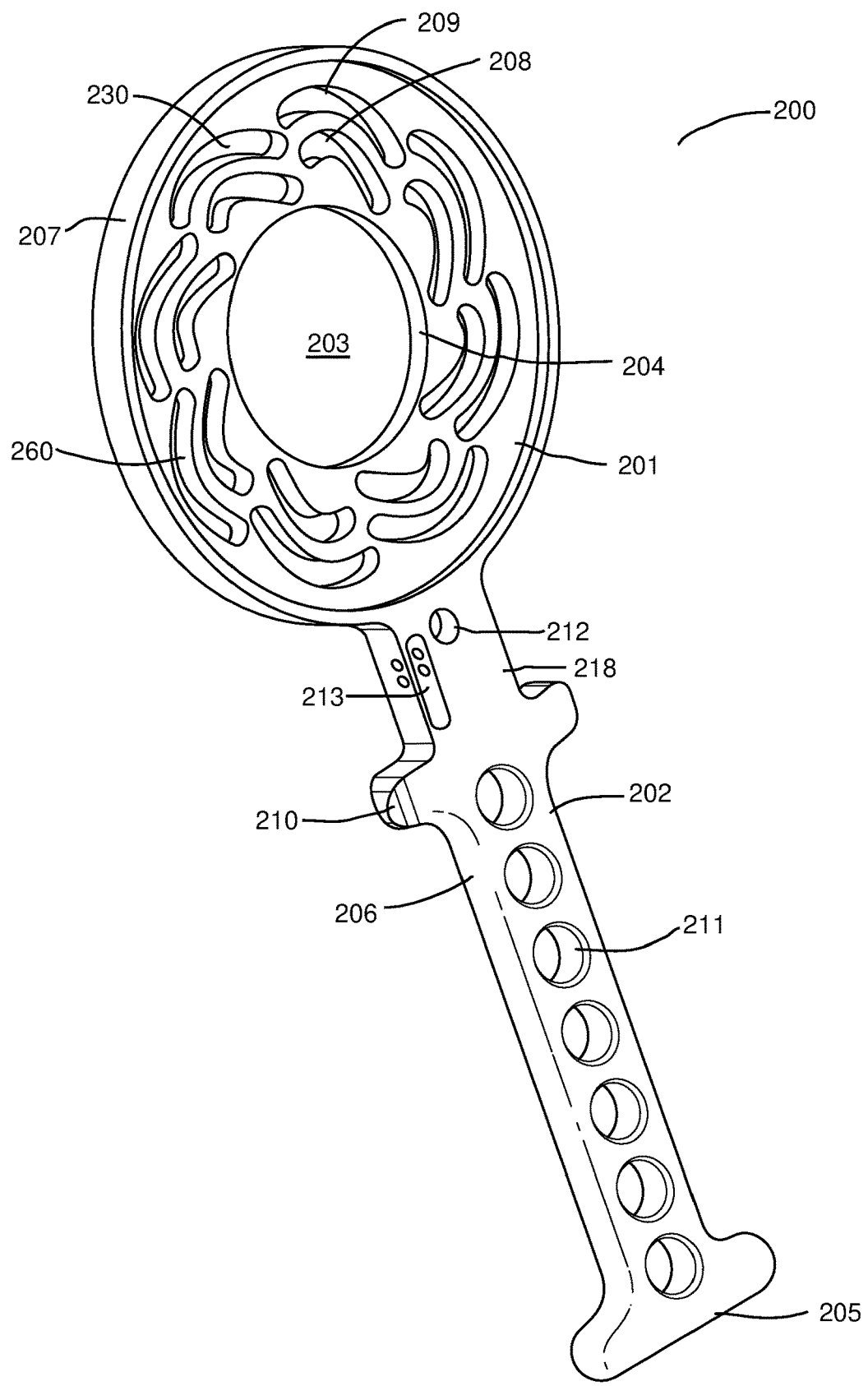
FIG. 4 illustrates another perspective view of the guide plate consistent with at least one embodiment of the present disclosure.

Referring to FIGS. 3 and 4, guide plate 200 is shown. Guide plate 200 is preferably in the shape of a disc, including volume sufficient to encompass a portion of the blades 100, or a blade assembly holder 400 thereof. Guide plate 200 defines a plane 240. Plane 240 is preferably perpendicular longitudinal axis 104 of blades 100. Guide plane 200 may be made of a sturdy material, such as metal, preferably stainless steel for sanitary purposes, plastic, ceramic, or other sturdy material. Guide plate 200 is formed via base 201 and, in some preferred embodiments, may contain handle 202 set off in one direction, preferably in plane 240. Guide plate base 201 planar body may be circular (as shown), ovular, square, or another geometric shape and have a thickness 207 (circumferential edge, top side, bottom side, mating feature to top plate 300). Guide plate 200 may be coupled to handle 202. The guide plate 200 also preferably comprises main aperture 203 to allow access to surgical portal 160 through guide plate 200. Aperture 203 may include interior defined by aperture edge 204 to define a guide hole in communication with the channel/portal to provide access by a surgeon or surgical tool from outside body (when guide plate 200 is set along the skin surface of a patient, into the tissue, unobstructed as surgical portal 160 maintains a channel free of tissues to allow a path to access a surgical target on or near the ends of the blades 100 (preferably framed by blade tips 101 and sequestered by channel. Aperture 203 may be a central aperture set in the middle, or near center of guide plate base 201 or another non-central position such as further away from handle end 205. Other embodiments may not include the aperture 203, but allow access to surgical portal 160 apart from guide plate 200. The central aperture 203 forms the top end of a central cylindrical channel 220 which will serve as surgical portal 160 at surgical site 750.

Guide plate 200 may also contain a plurality of interior slots 208 and exterior slots 209 acting to define a predetermined path for blade ends, or holders to pass through. In the preferred embodiment, there may be one interior slot 208 and one exterior slot 209 per each blade 100. Any number of slots may be used, including a single slot, or three or more, and either one set of slots or more than two sets of slots are also acceptable in alternative embodiments. Both/either interior slots 208 and exterior slots 209 can be liner or, more preferably, nonlinear as shown. Slots 208 and 209 are preferably shaped and sized to facilitate contraction and expansion of the blade assembly 150 via a slot-and-follower mechanism. In a preferred embodiment, connector pins 403 may be coupled to each blade assembly holder 400, to cause blades to move in predetermined fashion (preferably while maintaining parallelism in longitudinal axis). Guide plate 200 causes blade assembly 150 to move according to the paths of the slots 208 and 209. As defined herein, "screws" may alternatively be labeled as "pins" and the two terms may be used interchangeably throughout this disclosure. While screws generally refers to a threaded bolt, this limitation is but one of many ways in which a screw or shoulder screw may be employed. These screws may be with threads or without threads (such as a nail) and are herein contemplated where screws or pins are used to refer to these coupling fastener features. "Pins" act to provide coupling, while each pin may include a shoulder, or other feature, to allow for complementary mating, or fixation, in slots or otherwise.

Figure 5:
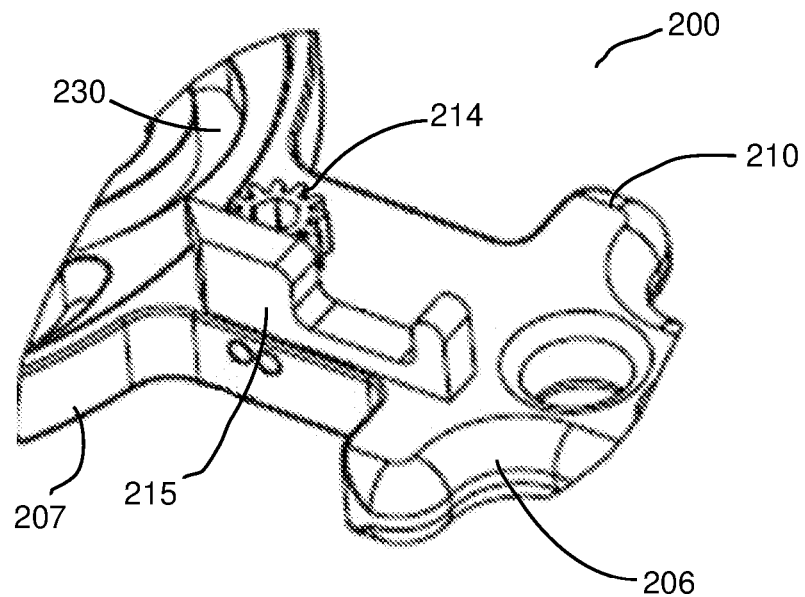
FIG. 5 illustrates a blown up view of the guide plate focusing on a pinion and pawl latch consistent with at least one embodiment of the present disclosure.

Handle 202 is optionally present in preferred embodiments of the invention extending outward in a coplanar direction from the guide plate base 201. Handle 202 generally comprises a thickness 206. Pinion mount 212 and pawl latch mount 213 may be housed or maintained on handle 202 top surface 218. In a preferred embodiment, the pinion mount 212 and pawl latch mount 213 engage guide plate 200 through top plate 300 via a pinion 214 and pawl latch 215 as shown in FIG. 5. The pawl latch 215 may be actuated by a spring-loaded system within handle 205 (not shown), by human force, by a combination of both or neither, or by a suitable alternative. There are also alternative solutions to engaging the guide plate 200 with the top plate 300, some of which are discussed in alternative embodiments of the present invention. Handle 202 may contain an additional ridge 210 and any number of apertures 211. Ridges 210 and/or apertures 211 may be used for a variety of purposes such as weight distribution, conforming to hand shape, holders for other surgical objects, a base for surgical equipment to clamp onto, maintaining arrangement of handle(s), or for aesthetic purposes.

Figure 6:
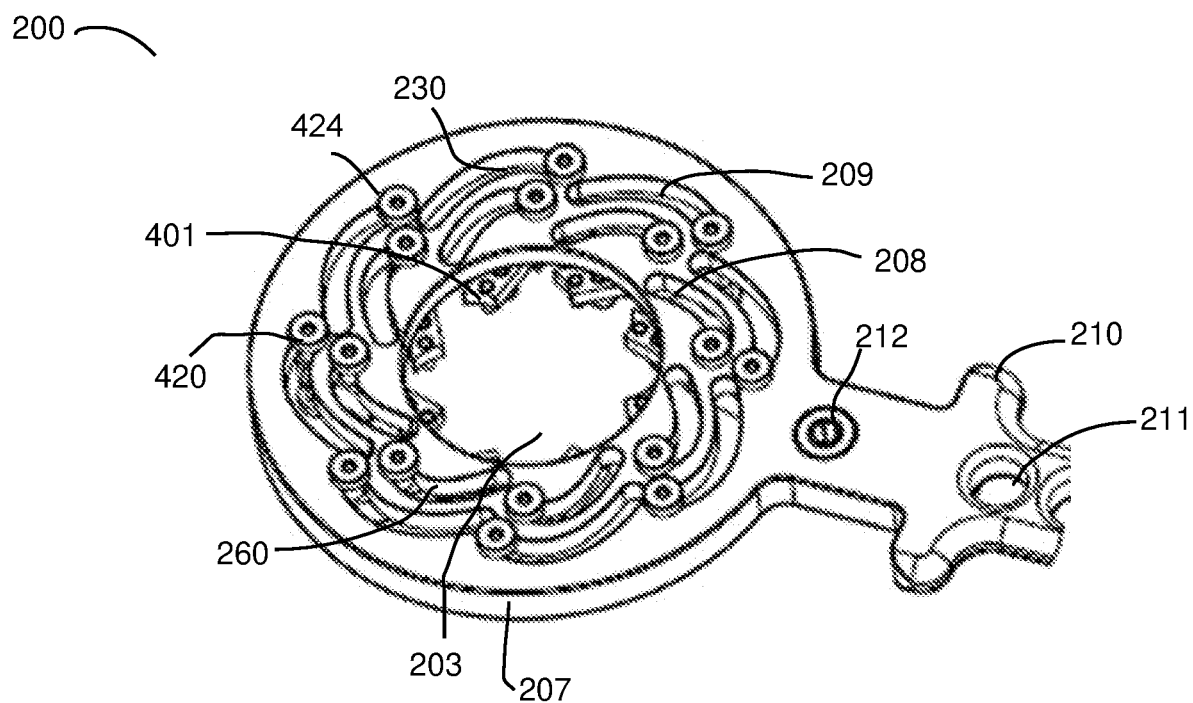
FIG. 6 illustrates another blown up view of the guide plate focusing on the tracking slots consistent with at least one embodiment of the present disclosure.
Figure 7:
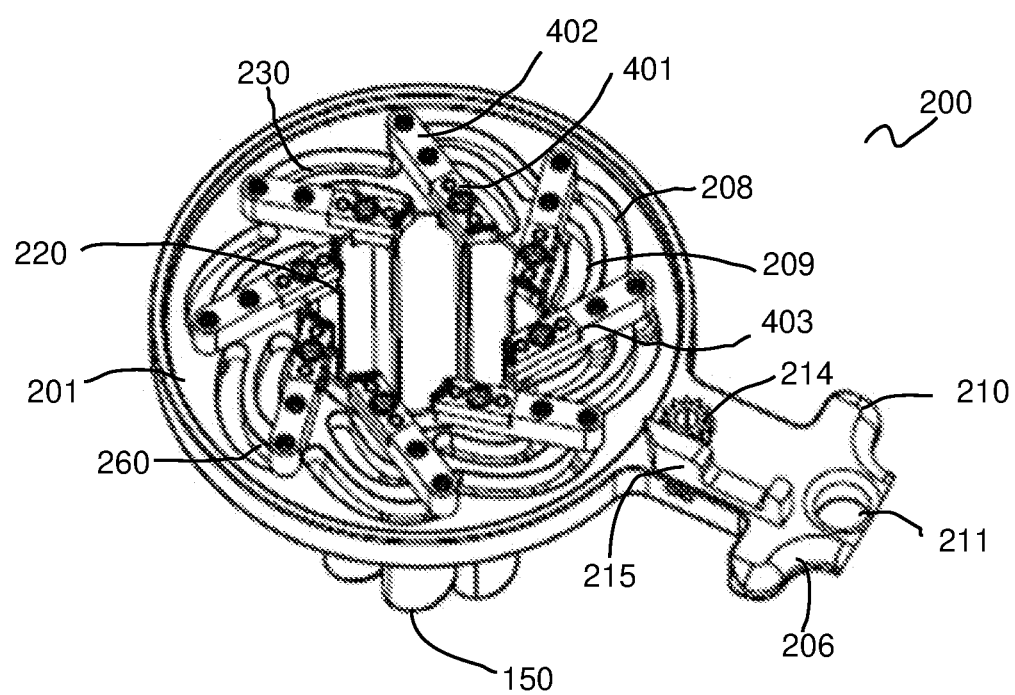
FIG. 7 illustrates another blown up view of the guide plate with the blade assembly attached consistent with at least one embodiment of the present disclosure.
Figure 8:
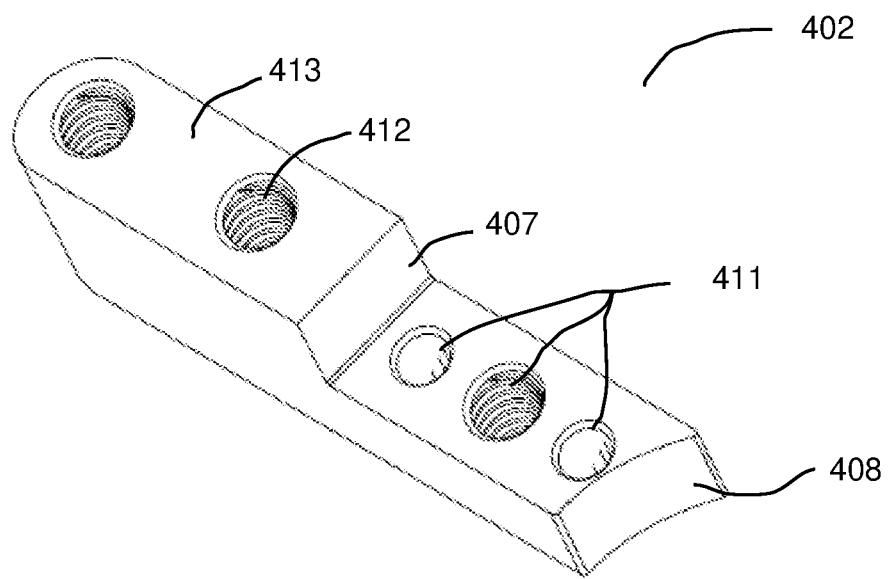
FIG. 8 illustrates a perspective view of the screw holder of the blade assembly holder consistent with at least one embodiment of the present disclosure.
Figure 9:
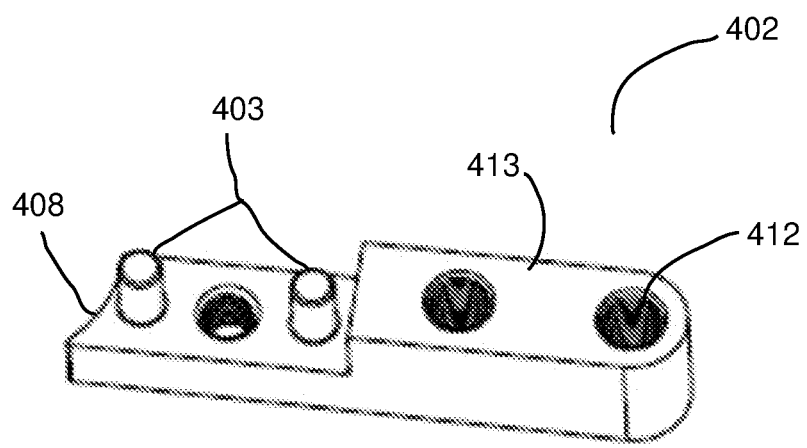
FIG. 9 illustrates another perspective view of the screw holder of the blade assembly holder consistent with at least one embodiment of the present disclosure.
Figure 10:
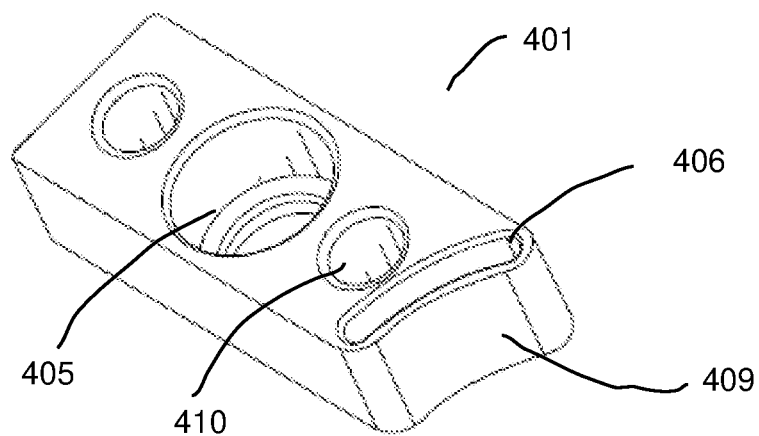
FIG. 10 illustrates a perspective view of the blade holder of the blade assembly holder consistent with at least one embodiment of the present disclosure.

Referring to FIGS. 6 and 7, guide plate 200 is shown coupled to blades 100 via blade assembly holder 400. In a preferred embodiment, blade assembly holders 400 are made in two separable parts, a blade holder 401 and a screw holder 402 as shown in FIGS. 8-10. Blade holder 401 and screw holder 402 are mated together by various means, an example of which may be via a bolt-type fastening mechanism through blade holder mating point 410 and screw holder mating point 411. In a preferred embodiment, both blade holder 401 and screw holder 402 have three meeting mating points 410 and 411 each, but any number of mating points is acceptable to fasten blade holder 401 to screw holder 402. Alternatively, blade holder 401 and screw holder 402 may be formed as a singular piece to form blade assembly holder 400 to couple blades 100 to guide plate 200. In alternative embodiments, blades 100 may be shaped or fastened to mate directly to guide plate 200, or to be bound by a fastener through guide plate 200. It is preferable that each blade 100 includes a curved end 122 along blade base 121 to blade holder assembly 400 to accommodate the blade assembly 150, shown by screw holder curved edge 408 and blade holder curved edge 409 in FIGS. 8-10. Blade 100 may include boss or tab 105 to mate with blade slot 406. Curved edges 408 and 409 are coplanar to but on the opposite end from the pin assembly housing 413. Pin assembly housing 413 comprises pin mounts 412. Pin mounts 412 may house shoulder screws 404 that can act as pins in interior slots 208 and exterior slots 209 of guide plate 200. Shoulder screws 404 include head 420 with a shoulder 424 that extends laterally over slot edges 260 to retain screws 404 in slots. Head and/or shoulder of pin(s) may serve on either or both the guide plate and/or top plate to secure the plates vertically, and prevent the plates form separating both vertically and laterally. Head with shoulder serves to provide a mushroom-head with a cap that extends over and beyond the slot on the outer surface to secure the plates. This can be seen in FIG. 2 as the heads extend over the slots. Further, as shown in FIG. 6, the head 420 and shoulder 424 may be set on and extend over the slot within the tool as between the guide plate shown, and the top plate (not shown, to be set upon the guide plate. The head and shoulder have a diameter greater than the slot, and the head/shoulder may be mounted onto the pin after placing the guide plate and top plate together and setting the pin therethrough, so as to secure the plates. Referring back to FIGS. 1-2, head 420 of pins may include indentation 415 or access point 414 to allow tool manipulation of screw when affixing screw into blade holder to secure within slot of guide plate/top plate. The outermost mount of pin mounts 412 may double as a mount for slots on guide plate 200, and tracking slot 310 on top plate 300. In a preferred embodiment, pin assembly housing 413 has at least two pin mounts 412.

Figure 24:
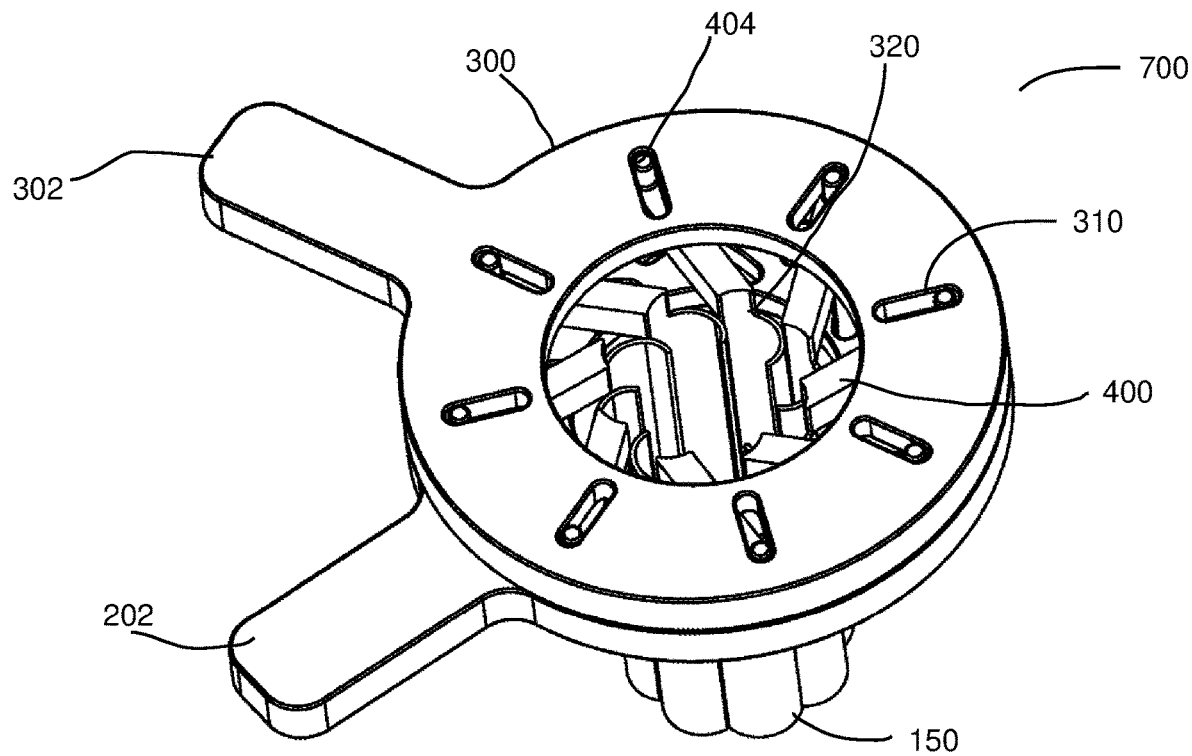
FIG. 24 illustrates a top perspective view of the surgical retractor system with the top lid consistent with at least one embodiment of the present disclosure.
Figure 26:
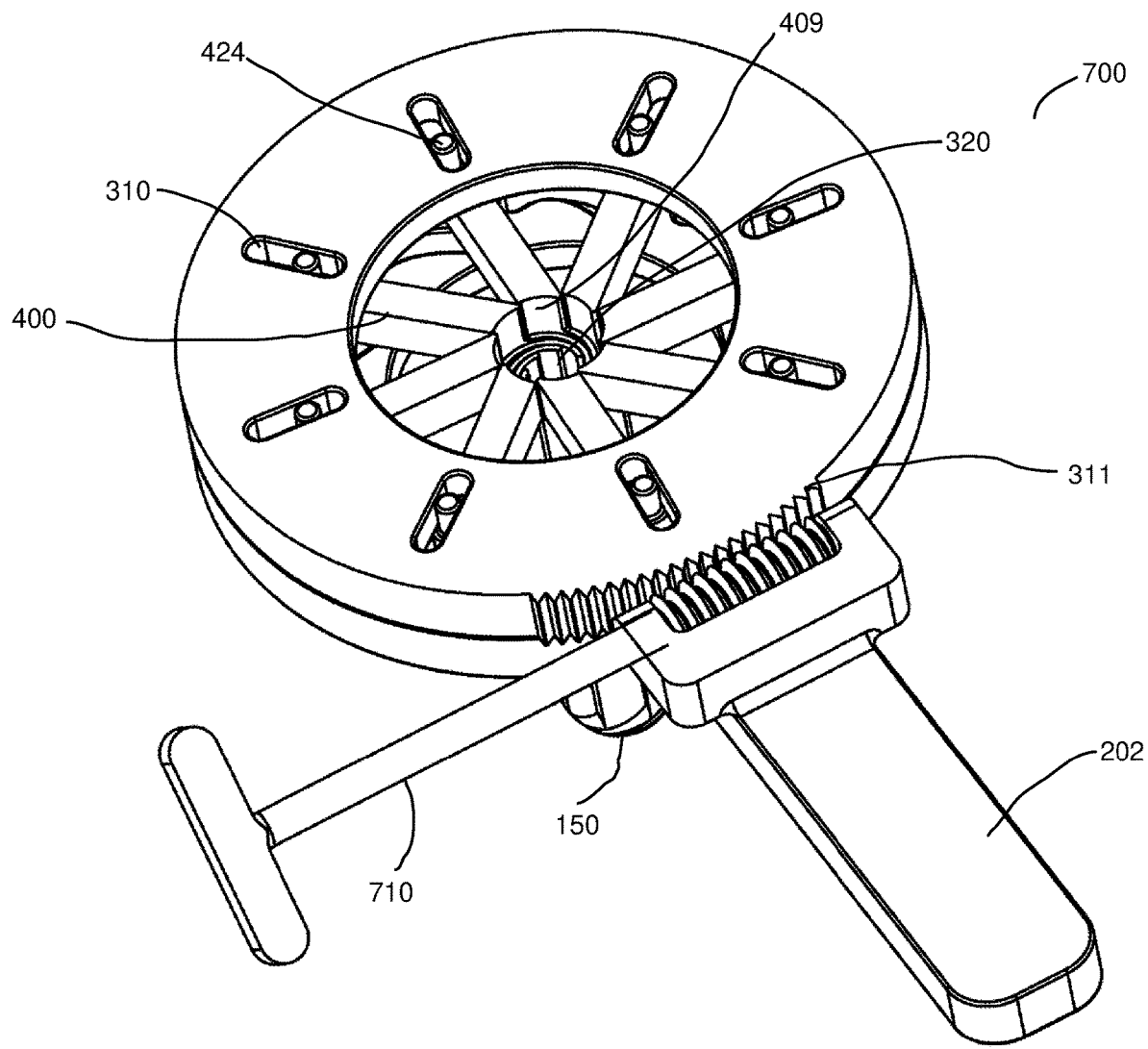
FIG. 26 illustrates a top perspective view of the surgical retractor system consistent with at least one embodiment of the present disclosure.
Figure 27:
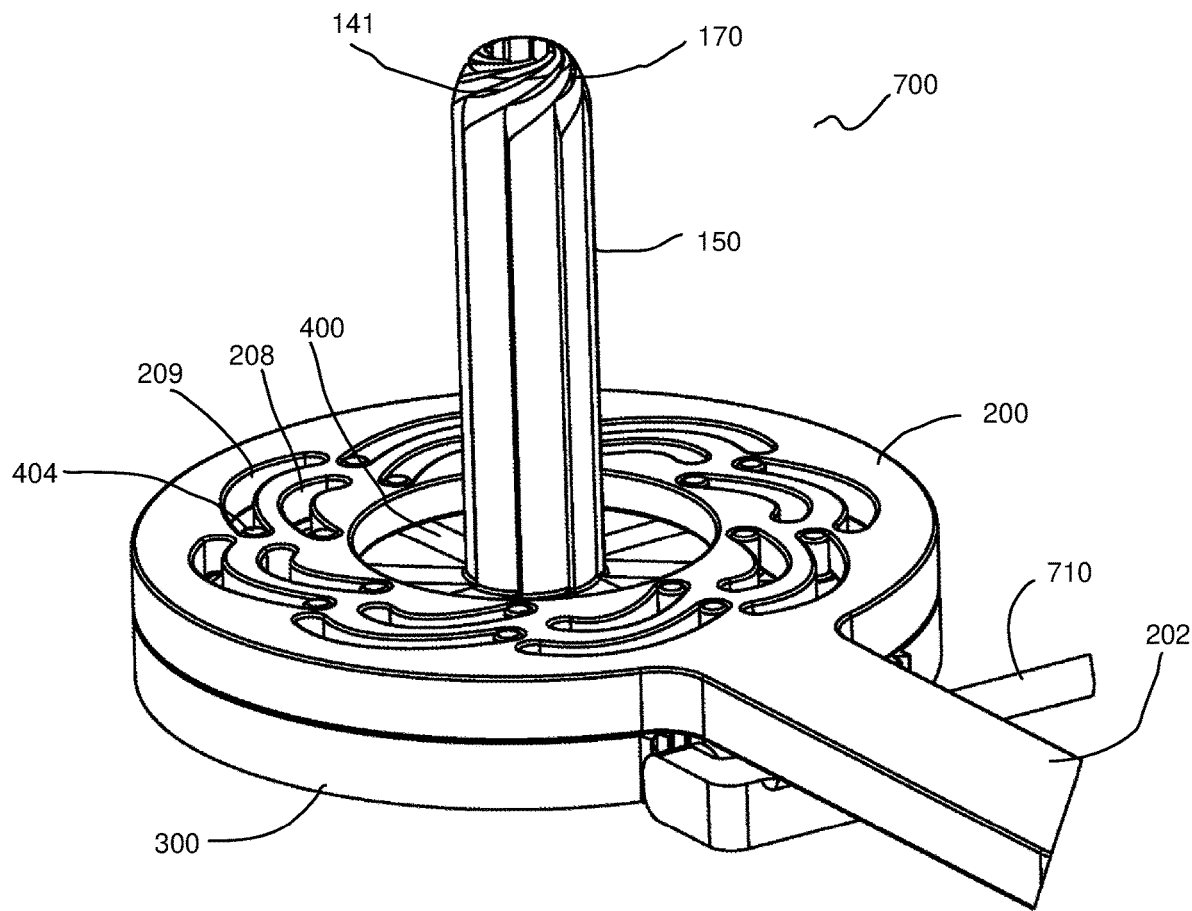
FIG. 27 illustrates a bottom perspective view of the surgical retractor system consistent with at least one embodiment of the present disclosure.

As shown in FIGS. 8-10, blade assembly holder 400 of a preferred embodiment may be in two pieces, a blade holder 401 adapted to mate with blades 100 and with screw holder 402. Blade holder 401 includes mating points 410 to receive connector pins 403 that are simultaneously passed through mating holes 411 in screw holder 402 and mating points 410. Pin mounts 412 are adapted to receive pins, or more preferably threaded screws, that will pass though guide plate slots (shown in FIGS. 6-7), while pin mount 412 in screw holder may house a further pin 424 set within pin mount 412 and radial slots of top plate 300 (as shown in FIGS. 24, 26, etc.). Dual pins 404 are set through pin apertures 405 to mount to guide plate (as shown in FIG. 27) and a single pin 424 may be used through may be used through pin mounts 412 in screw holder 402 to mate with top plate (as shown in FIG. 24).

Referring to FIG. 10, blade holder 401 preferably has a blade slot 406 curved to match blade holder curved edge 409 as well as blade 100. As shown in FIG. 26, curved edges 409 form a near circle acting as portal access that matches the curvature of overlapping blades (here shown in a contracted state). The blade slot preferably penetrates through the blade holder 401, but need not penetrate completely through. Alternatively, the blade slot 406 may or may not be sealed after being coupled to blade 100. The blade slot 406 is preferably nonlinear, but may be linear in other designs to reflect the shape of the blade 100. Each blade 100 is coupled to a blade assembly holder 400 via the blade slot 406 and blade holder 401.

Figure 11:
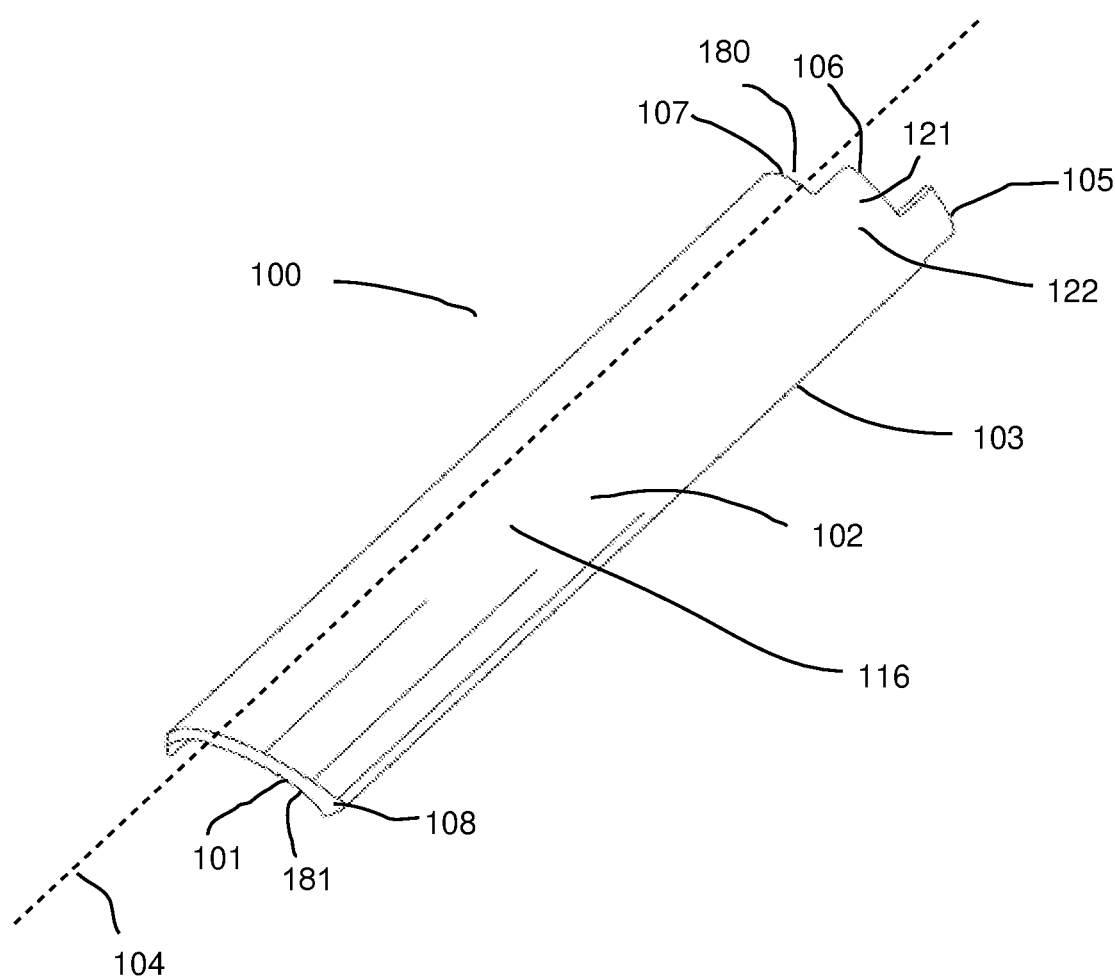
FIG. 11 illustrates a perspective view of the blade consistent with at least one embodiment of the present disclosure.
Figure 12:
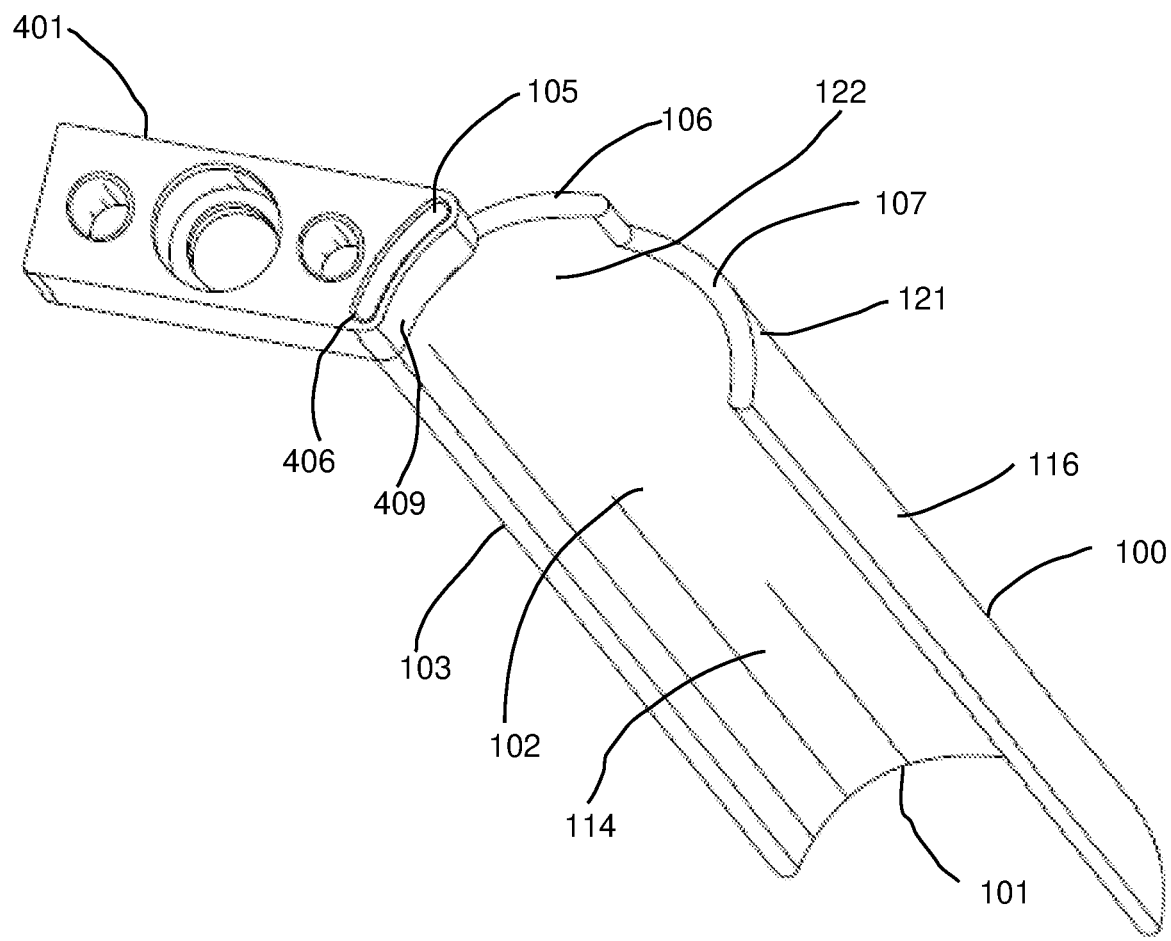
FIG. 12 illustrates a perspective view of the blade attached to the blade holder consistent with at least one embodiment of the present disclosure.

Referring to FIG. 11, a preferred embodiment of blade 100 is shown. Blade 100 is preferably made of stainless steel or another surgically appropriate material. Blades 100 generally are shaped with length 103, width 108, and shelf 107 and blade curved end 122 at base 121 and have an interior side 114 and an exterior side 116. Each blade 100 provides a longitudinal axis 104 in parallel with other blades 100 parallel axes, and the blades 100 all may have a curvature 102. The longitudinal axis 104 may also act as a revolve axis for each blade 100. Shelf 107 of blade top serves to define proximal end 180 of blade 100. Blade 100 has distal end 181 opposing the proximal end 180. Blade base 121 may include tab 105, and ridge 106 adapted to help mount either directly or indirectly into a guide plate 200. Alternative embodiments of the blade 100 may or may not include curvature 102, tab 105, ridge 106, and/or any combinations thereof. Additionally, alternative embodiments may contain blade 100 with tip 101 that is jagged, pointed, or another desired shape best suited to penetrate at surgical site 750. Tip 101 may serve as distal end 181. In a preferred embodiment, blade 100 has a ridge 105 that mates with blade holder 401 at blade slot 406, as shown in FIG. 12. Preferably, blades 100 share a similar longitudinal curvature 102 allowing for blades 100B to more easily overlap with neighboring blades 100A and 100C (for example) and in blade assembly 150 as shown in FIGS. 15-22. In an alternate embodiment, blades 100 may be flat or non-curved and blades 100 may be assembled in another fashion to create a surgical portal 160.

Blade ridge 106 present in some embodiments of the invention may be used to prevent blades 100 from intersecting each other during contraction 151 and expansion 152 of blade assembly 150.

Figure 13:
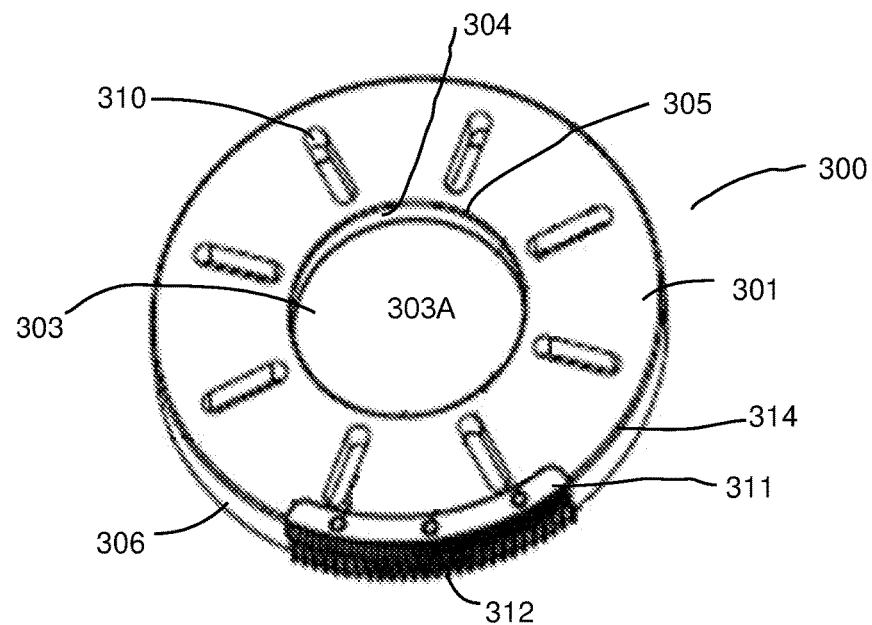
FIG. 13 illustrates a top view of the top plate consistent with at least one embodiment of the present disclosure.
Figure 14:
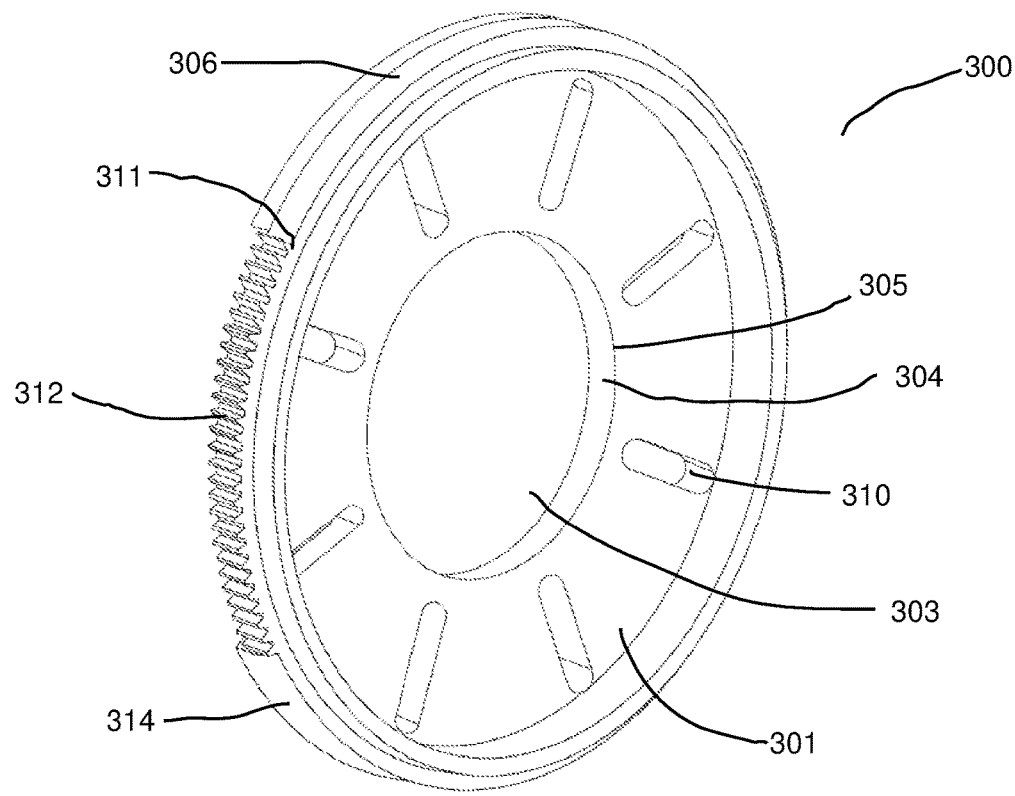
FIG. 14 illustrates a side view of the top plate consistent with at least one embodiment of the present disclosure.

An embodiment of the top plate 300 is represented by FIGS. 13-14. Top plate 300 may mate with guide plate 200 to provide for a blade actuating tool. Opposite side of top plate 300 is top plate base disc 301 with side edge 306 set circumferentially thereon. Top plate 300 mates with guide plate 200, and space 765 set therebetween provides for functioning and moving parts of blade actuating mechanism to be contained therein. Preferably top plate 300 and guide plate 200 are of a similar size and shape to allow complementary mating. Top plate 300 is preferably circular in shape, but can be any round shape or any polygon and may not be completely restricted by the shape of the guide plate 200. Top plate 300 preferably includes access to channel via main aperture 303 with an aperture interior 304, defined by aperture edge 305 defining a guide hole. Preferably, central aperture 303 is a symmetric circle surrounding a virtual center. Aperture 303 may be a central aperture set in the middle, or near center of top plate 300, or another non-central position. Other embodiments may not include the aperture 303, but allow access around top plate 300. Central aperture 303 may be designed to allow portal access 320 for the surgical portal 160 at surgical site 750.

Top plate 300 preferably includes tracking slots 310 at a number equal to the number of blade assembly holders 400, although an alternate number of tracking slots 310 may be contemplated. Tracking slots 310 may be linear (as shown) or nonlinear or a combination of the two. Tracking slots 310 do not need to correspond to the guide plate 200 interior slot 208 and exterior slot 209 in terms of shape. In the preferred embodiment, the guide plate 200 slots 208 and 209 are nonlinear and the top plate slots 310 are radial and linear extending from center 303A in a symmetric manner. In the preferred embodiment, the top plate slots 310 extend outwardly from the aperture 303, and correspond with the movement of the blade assembly holders 400 as the top plate 300 is rotated relative to the guide plate 200. This is contrary to how the guide plate 200 interior slots 208 and exterior slots 209 are in relation to the guide plate aperture 203. In the preferred embodiment, the disparity in slots relative the guide plate 200 and the top plate 300 allows for the blade assembly 150 to contract 151 and expand 152 in a spiral fashion as the plates are rotated relative one another. Guide plate 200 remains fixed relative the patient body 720, while the top plate 300 is rotated, thus pulling the blade ends or holders 400 radially outward, while a vertical pin may pass through the slots in both plates simultaneously as the plates rotate one another. Other designs of the slots may allow the blade assembly 150 to expand 151 and contract 152 in a different manner.

Alternative drive mechanisms for the opening and closing, expanding and contracting, of the blade assembly 150 are now discussed. Top plate 300 may feature a partial spur gear 311 with teeth 312 mounted along an circumferential edge 314 of top plate 300. Partial spur gear 311 is preferably situated on a partial portion of the circumferential edge 314 of top plate 300. Spur gear teeth 312 may interact with pinion 214 mounted on handle top surface 218. Pawl latch 215 interfaces with teeth 312 to lock relative orientation of top plate 300 with guide plate 200 to fix the diameter of the blade assembly and channel. In alternative embodiments, other methods may be applied to achieve such an interaction. Top plate 300 may secure blade assembly holder 400 between guide plate 200 and top plate 300. Top plate 300 may interact with guide plate 200 to allow twisting or rotation of top plate 300 while maintaining coaxial contact with guide plate 200 thereby moving blade assembly 150 through the slots 208, 209, and 310 via screw holder 402 and allowing blade assembly to contract 151 and expand 152.

This movement may be driven via a variety of methods, one of which includes manually moving top plate 300 while simultaneously pulling pawl latch 215 away from top plate 300 to disengage teeth lock, thereby allowing pinon 214 to interact freely with partial spur gear 311. By this method, pawl latch 215 may then be released to mate again with partial spur gear 311 at a specific tooth 312 to lock relative orientation and achieve a desired diameter for the blade assembly 150 and surgical portal 160. The multitude of teeth 312 in spur gear 311 may allow user to incrementally change the shape and size of the blade assembly 150 to provide the preferred diameter of channel via contracted 151 or expanded 152 shapes, as desired. Preferably, the blades 100 are contracted 151 when entering the incision into body, and thereafter expanded 152 to push tissues out of the way and provide access to surgical site 750 through surgical portal 160.

Referring to FIGS. 15-22, blade assembly 150 is shown in various states as it expands from both contracted 151 to expanded 152 states, or vice versa. FIG. 15 shows blade assembly 150 in contracted 151 state. Each blade 100, for example 100B overlaps neighboring blade 100C, and is in turn overlapped by neighboring blade 100A on opposite side. The overlap of blades is maximized in contracted state 151 in order to draw down diameter of channel and make the insertion (and removal) of tool from surgical incision/cavity more discreet. Once in place (within body cavity), blade assembly 150 may be expanded to push tissues apart, in a preferable circular portal 154, to provide access to tissue/surgical site 750 deep within patient body 720 through aperture in guide plate/top plate (not shown). In a preferred embodiment, each blade 100 is set with a longitudinal axis parallel its neighboring blades, while perpendicular a plane of the guide plate 200 (not shown), and each blade 100 has a curvature 102 to facilitate overlapping, the curvature arc-radius is related to the number of blades. Preferably, blades are each in contact with adjacent blades from the distal end to the proximal end, preferably in both open and closed positions, and preferably as the blades transition between open and close, and vice versa. As the number of blades 100 is increased, the arc-radius increases for a more flat curvature 102, while as the number of blades 100 may be reduced in alternative embodiments, the curvature 102 may be increased and the arc-radius decreased to make curvier blades 100. As shown in FIGS. 15-22, blade assembly 150 provides manipulatable overlapping circular formation 110 wherein each blade 100B maintains tangential contact with an adjacent blade 100A and 100C, wherein each blade overlaps 110 another, the overlap 100 decreasing as the blade assembly is expanded 152. Overlap 110 allows for each blade 100 to comprise an overlap exterior edge 112 and an interior edge 111. Cylindrical channel 154 may be formed by the exposed interior edges 111 of each blade 100.

FIG. 16 demonstrates blade assembly 150 in expanded 152 state. As in FIG. 15, each blade 100 maintains tangential contact with adjacent or neighboring blades 100 on both sides. Each blade 100 includes exterior edge 112 and interior edge 111, each of the edges in contact with neighboring blades 100. In some embodiments, in expanded state 152, the blades 100 may separate to provide maximum channel radius. In other embodiments, described below relative a sleeve embodiment, the blades 100 may not be in contact with each neighboring blade 100, and provide gaps (not shown) that can be covered by sleeve or sheath. Channel 154 widens to form surgical portal 160, and shape of 'cylinder' modifies from a more perfect cylinder to a less perfect cylinder, such as a vertically- or longitudinally-ribbed tube 156 in expanded 152 state.

FIGS. 17-22 demonstrate an embodiment of the blade assembly 150 having eight (8) blades. Beginning in a contracted 151 state, FIG. 17 demonstrates blades 100, wherein each blade 100B is set next to neighboring blades 100A and 100C with interior side 114 abutting neighboring exterior side 116. As demonstrated in FIGS. 18-19, as the blade assembly expands (shown step wise FIG. 17→18→19→20→21→22, even though the expansion should be smooth as blades move through tracks in guide plate), preferably, blade sides remain in contact with neighboring blades. Most preferably, an interior edge 111 interfaces with neighboring exterior side 116. In alternative embodiments, exterior edge 112 may interface with interior side 114 (not shown). As blade assembly 150 orientation is modified, blade assembly 150 can form alternate states between the most contracted 151 state and most expanded 152 state. As necessary for access through surgical portal 160, the diameter of cylindrical channel 154 may be determined and set (via pawl, not shown), to lock a predetermined size of channel diameter.

Figure 23:
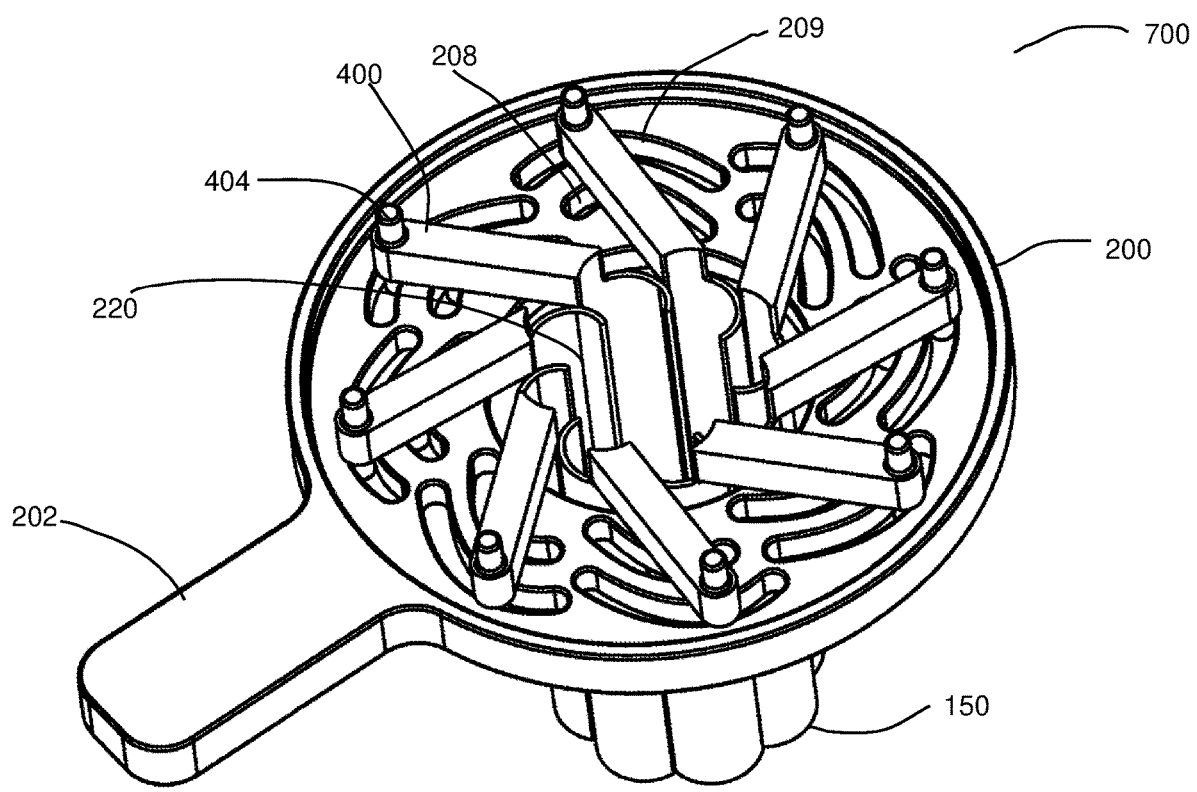
FIG. 23 illustrates a perspective view of the surgical retractor system without the top lid consistent with at least one embodiment of the present disclosure.
Figure 25:
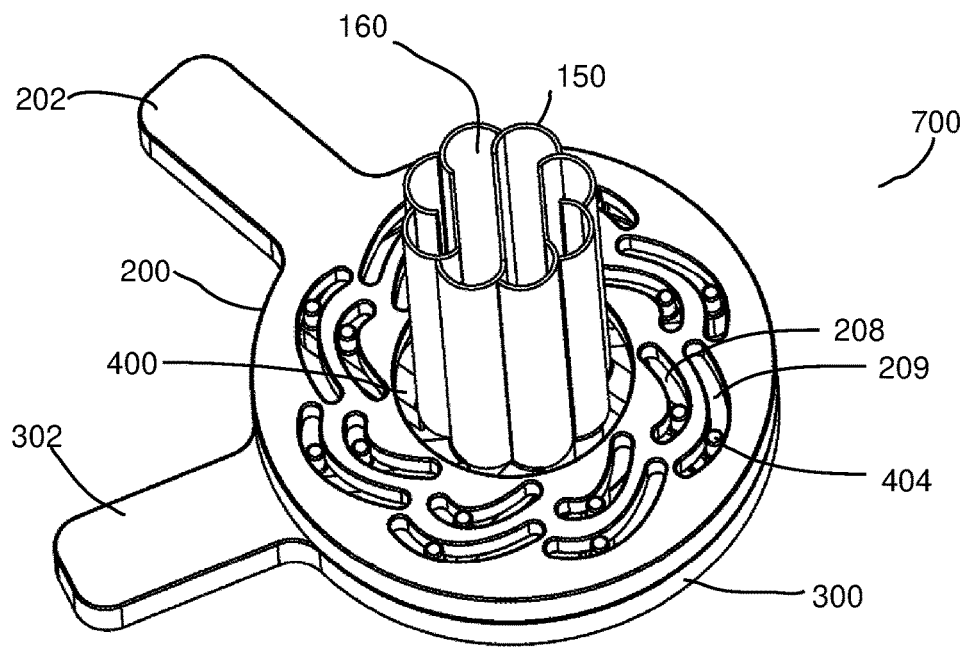
FIG. 25 illustrates a bottom perspective view of the surgical retractor system with the top lid consistent with at least one embodiment of the present disclosure.

FIGS. 23-25 show an embodiment of the surgical retractor system 700 that can allow for the user to manually move top plate 300 and guide plate 200 relative one another by means for two handles 202 and 302. As the handles 202 and 302 are rotated relative one another, this causes the guide plate 200 and top plate 300 rotatably coupled one another to rotate relative one another and force pins/screws in slots to move. As the pins/screws are coupled to the blades 100, the relative rotation of the handles 202 and 302 causes the blades to contract and expand. FIG. 23 illustrates the surgical retractor system guide plate 200 and handle 202 along with the exposed blade assembly holders 400 coupled with blades 100 and slots 208 and 209 set within the tool with top plate 300 removed. An alternative embodiment of the guide plate 200 is shown with interior slots 208 and exterior slots 209 and a handle 202. An alternative embodiment of the blade assembly holder 400 is shown with shoulder screws 404 or alternatively, pins 404. The pins 404 are present on top side and the underside of the blade assembly holder 400 to interact with the guide plate 200 via interior slots 208 and exterior slots 209 and, if necessary, the top plate 300 slots 310. The blade assembly holders 400 assembled in this way allow for the blade assembly 150 to contract 151 or expand 152 as desired and forming a central cylindrical channel top end 220. FIGS. 24-25 show a similar embodiment, with a top plate 300 coupled with a top plate handle 302, illustrating top slots 310. In this embodiment, the user is free to contract 151 and expand 152 the blade assembly 150 manually and access the surgical site 750 via the top plate portal access 320.

FIGS. 26-27 show yet another embodiment of the surgical retractor system 700. In this embodiment, a worm gear 710 is used alongside the spur gear 311 to rotate top plate 300 relative guide plate, in order to cause pins 404 set in slots in both the guide plate 200 and the top plate 300 to move through the slots and thus cause the positions of contracted 151 or expanded 152 blade assembly 150. As worm gear 710 is turned in a first direction the top plate 300 is rotated relate the guide plate 200 to open/expand the blade assembly 150 as the top plate 300 pins 424 are pushed radially outwardly in tracking slots, while guide plate 200 remains stationary and fixed to handle 202. Blade holders 401 cause concurrent movement of shoulder screws 404 in interior and exterior slots 208 and 209 to move outwardly from center of aperture 203 and thus cause the expansion of the blade assembly 150. Turning worm gear 710 drive in the opposite direction causes the opposite movement in the pins 424 and screws through the slots and thus contracts the blade assembly 150. An embodiment of the invention as shown in FIGS. 26-27 illustrates blade assembly 150 with blades 100 having blade tips 101 with angled tips 141 causing the multitude of blades combined to form a bullet nosed edge 170 in aggregate. This may be achieved by altering the geometry of each blade 100 at blade tip 101 to achieve a desired angle of attack and shape to allow blade assembly 150 in contracted shape 151 to better penetrate the incision site 740 and reach the surgical site 750.

Figure 28:
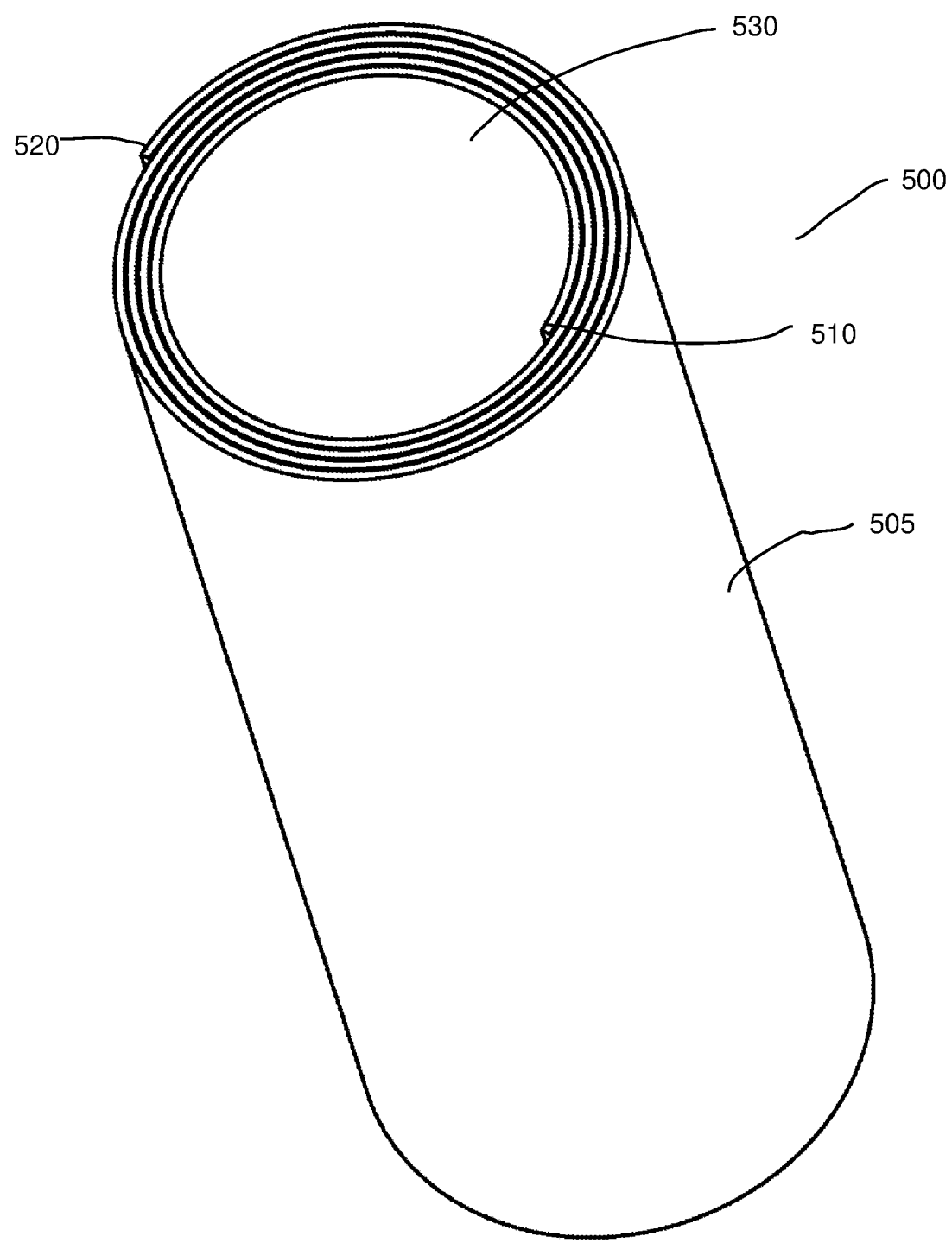
FIG. 28 illustrates a protective sleeve consistent with at least one embodiment of the present disclosure.
Figure 29:
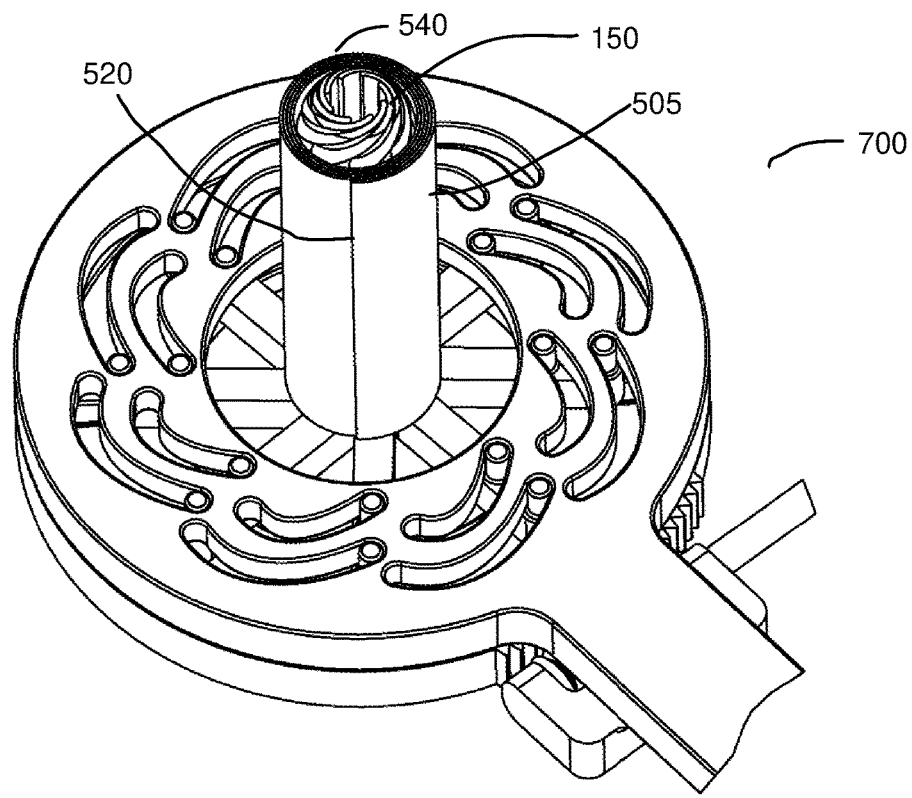
FIG. 29 illustrates a bottom perspective view of the surgical retractor system consistent with at least one embodiment of the present disclosure.
Figure 30:
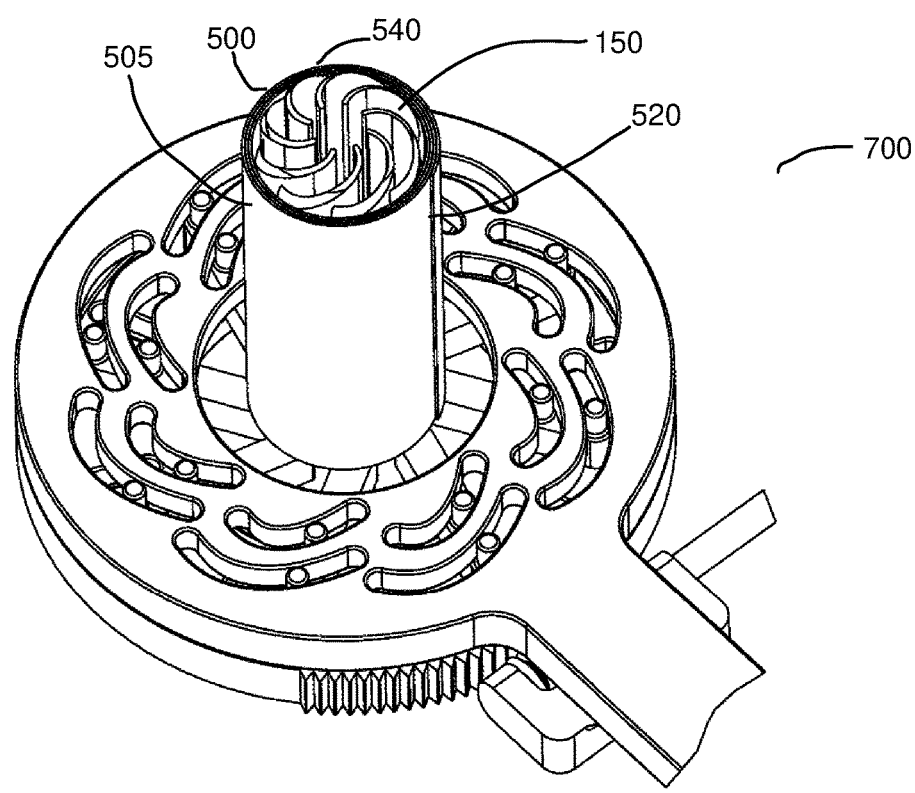
FIG. 30 illustrates a bottom perspective view of the surgical retractor system consistent with at least one embodiment of the present disclosure.
Figure 31:
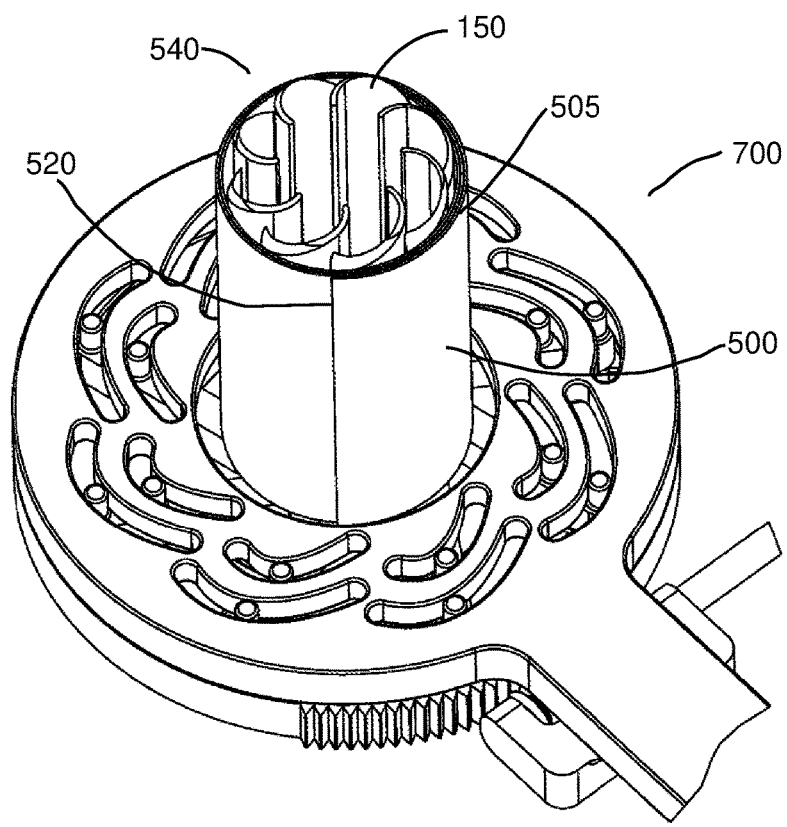
FIG. 31 illustrates a bottom perspective view of the surgical retractor system consistent with at least one embodiment of the present disclosure.
Figure 32:
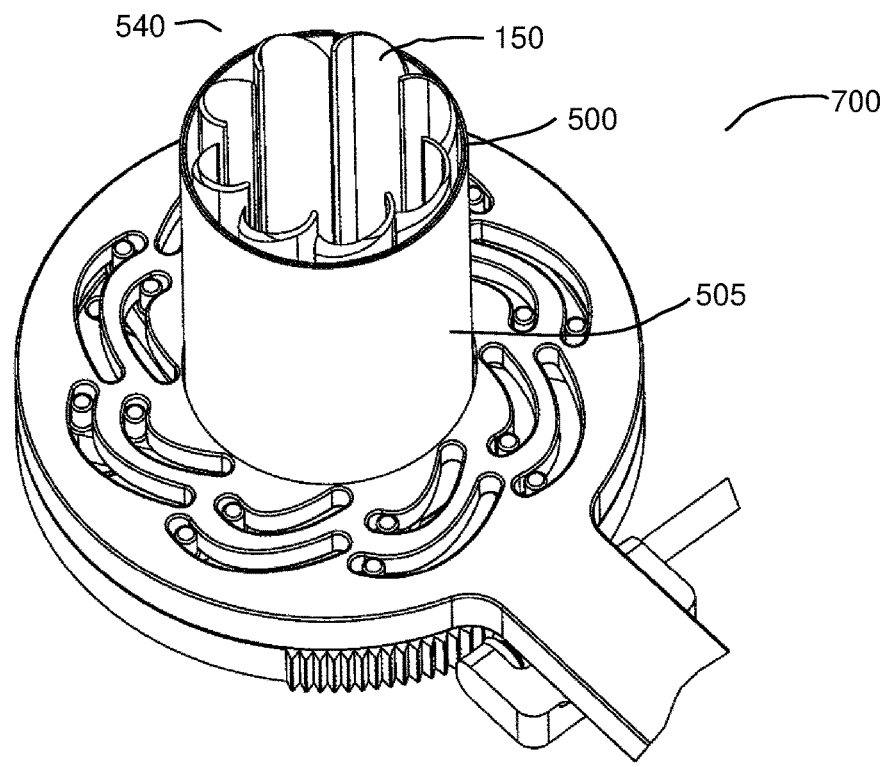
FIG. 32 illustrates a bottom perspective view of the surgical retractor system consistent with at least one embodiment of the present disclosure.

FIG. 28 shows a protective sleeve 500 which is another feature of the surgical retractor system 700. This sleeve 500 may be comprised of a rolled-up piece of thin plastic sheet, however in alternative embodiments, sleeve may be a single tube of flexible material. Sleeve prevents potential pitching of tissues between blades upon expansion, but more importantly upon retraction or contraction of blade assembly within cavity of patient. The material of the plastic sheet should be flexible and have a low coefficient of friction. Some materials of such sleeve may include plastics, such as polytetrafluoroethylene (PTFE), known by the brand name Teflon®, ultra-high-molecular-weight-polyethylene (UHMWPE), latex, or shape memory metal (alloys), or another suitable material that is flexible enough to expand or unravel as the blades are expanded relative one another. Preferably, sleeve 500 provides a liquid-tight seal around the blades to prevent fluids from entering the surgical portal. The spring tension in the rolled-up sleeve 500 maintains the diameter of the roll smaller than the diameter of the retractor blades when it is in the free state. The sleeve comprises an exterior 505, an interior end 510, and exterior end 520, and a channel 530. A purpose of the sleeve 500 is to protect the surgical site 750 from any unwanted internal tissue seeping into the surgical site 750. FIGS. 29-32 show an embodiment of the surgical retractor system 700 with the addition of the protective sleeve 500. Sleeve 500 also prevents direct contact of blades 100 with tissues in the patient cavity and prevents pinching of cutting of tissues as the blade assembly 150 is expanded 152 or contracted 151. As the blade assembly 150 contracts 151 and expands 152, the sleeve 500 will keep simultaneous contact with the blade assembly 150 via unraveling coiled sleeve 540. Preferably, sleeve 500 is wrapped in a direction of the blade expansion to prevent sleeve exterior end 520 from catching on tissues as the blade assembly is expanded within the patient cavity. However, the wrapping direction of the sleeve may be reversed as may be required for any specific surgical need.

Figure 33:
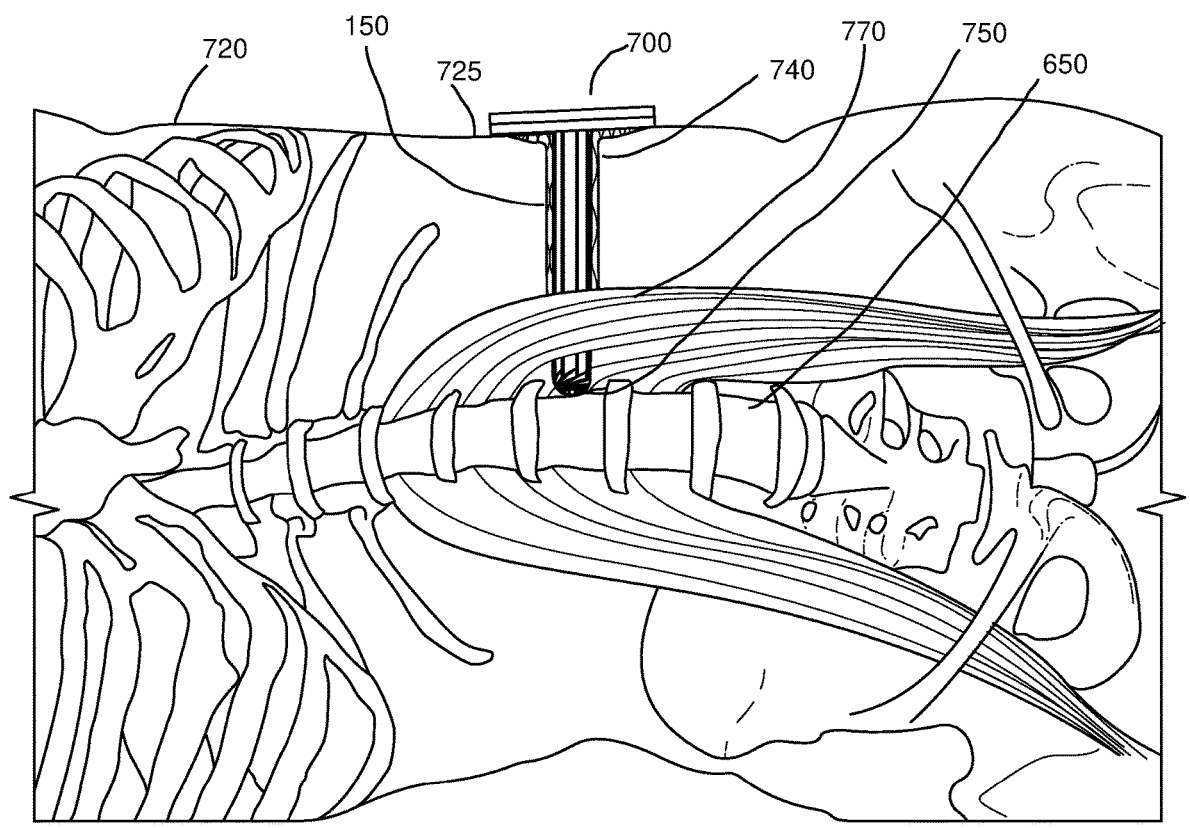
FIG. 33 illustrates a side perspective of a human anatomy with the surgical retractor system inserted laterally consistent with at least one embodiment of the present disclosure.
Figure 34:
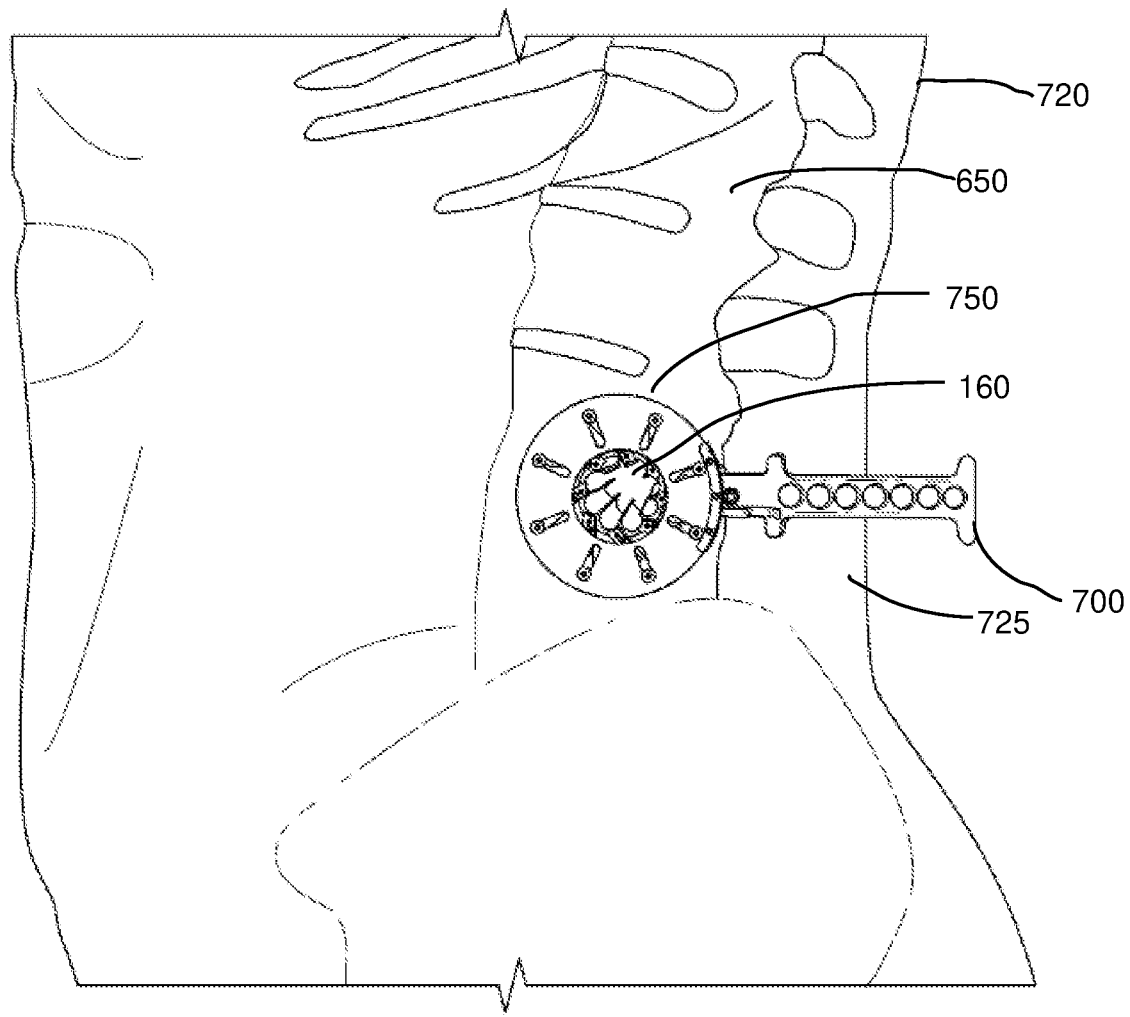
FIG. 34 illustrates a top perspective of a human anatomy with the surgical retractor system inserted laterally consistent with at least one embodiment of the present disclosure.

FIGS. 33-34 show an embodiment of the surgical retractor system 700 at the surgical site 750. Patient 720 is preferably anesthetized with general or local anesthetic, or as otherwise known in the art for spinal surgery or other surgery for which the tool will be used. Patient, lying on side exposes abdomen 725 for incision at incision site 740. Cavity 730 may be initially expanded/created with hands or other tools to provide space for uncontracted blades assembly to enter. Alternative, contract blade assembly may be placed into incision site 740 to cause initial cavity. As blade assembly is expanded within cavity 730 cavity expands to provide surgical portal 160 through channel 154. The blade assembly 150 penetrates the internal material including the psoas muscle 770 to reach the desired surgical site 750 at the spine 650. Then, a surgical portal 160 is opened allowing the surgeon to operate at the surgical site 750 without any interference from internal material due to the protection of the sleeve 500 and the overlapping formation 110 of the blade assembly system 150.

Figure 35:
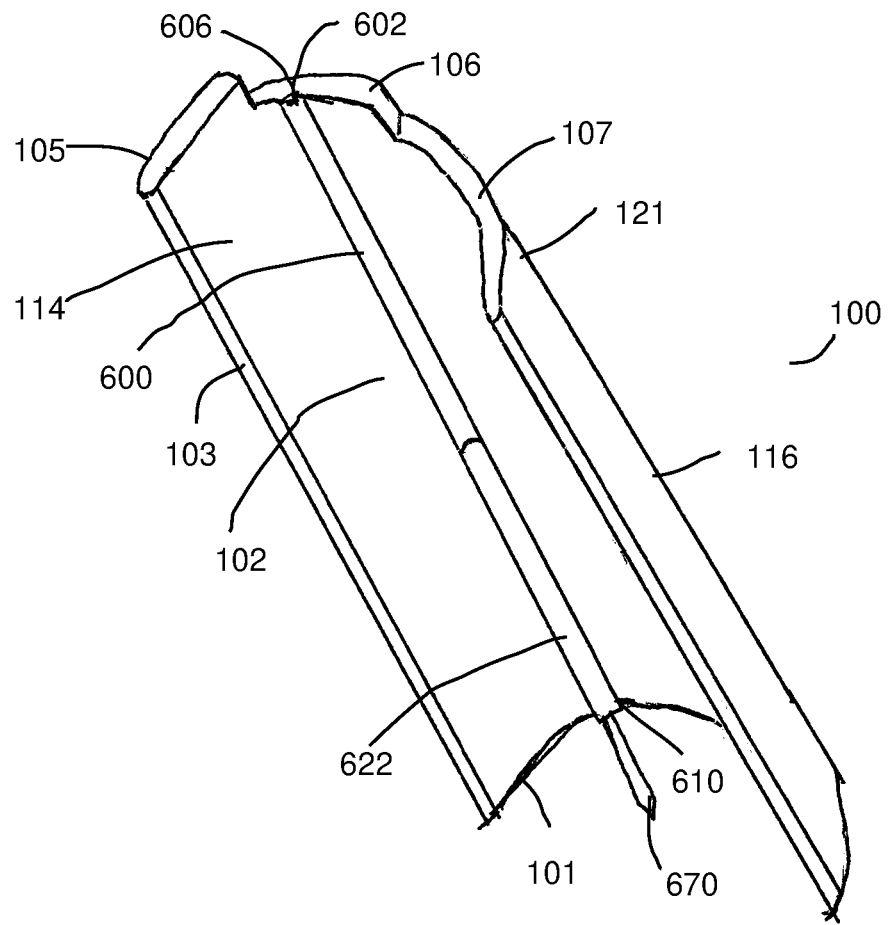
FIG. 35 illustrates a top interior perspective view of a blade consistent with at least one embodiment of the present disclosure.
Figure 36:
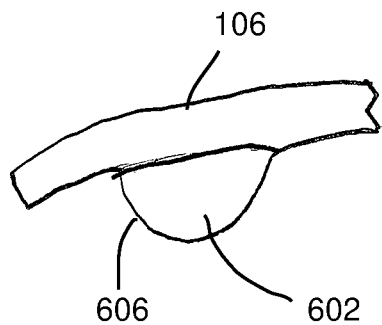
FIG. 36 illustrates a top plan view of a blade consistent with at least one embodiment of the present disclosure.
Figure 37:
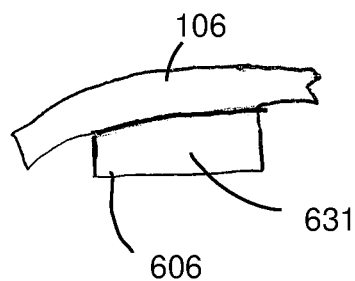
FIG. 37 illustrates a top plan view of a blade consistent with at least one embodiment of the present disclosure.
Figure 38:
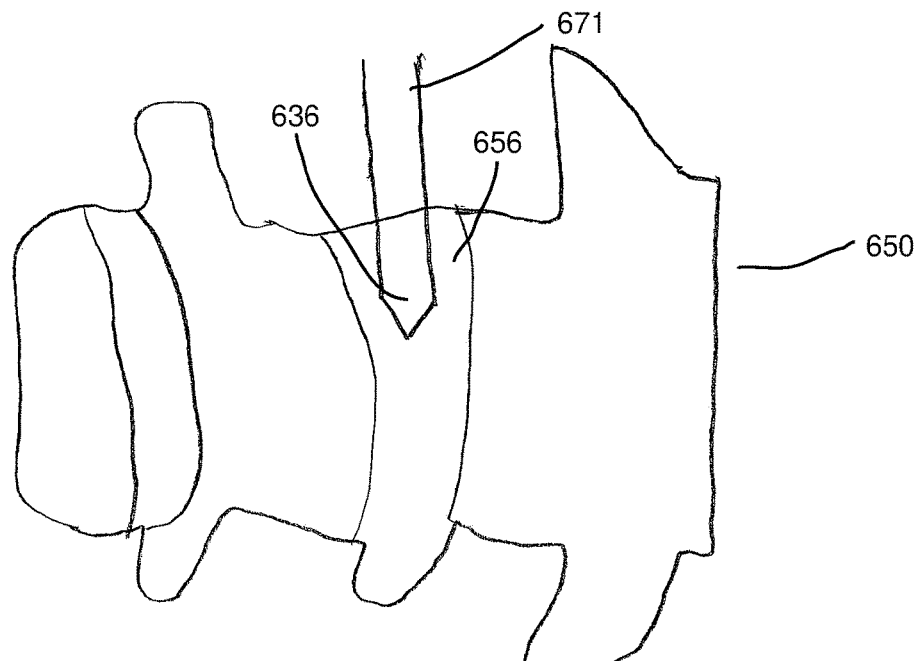
FIG. 38 illustrates an anterior view of a spine with a shim embodiment mounted lateral thereon consistent with at least one embodiment of the present disclosure.
Figure 39:
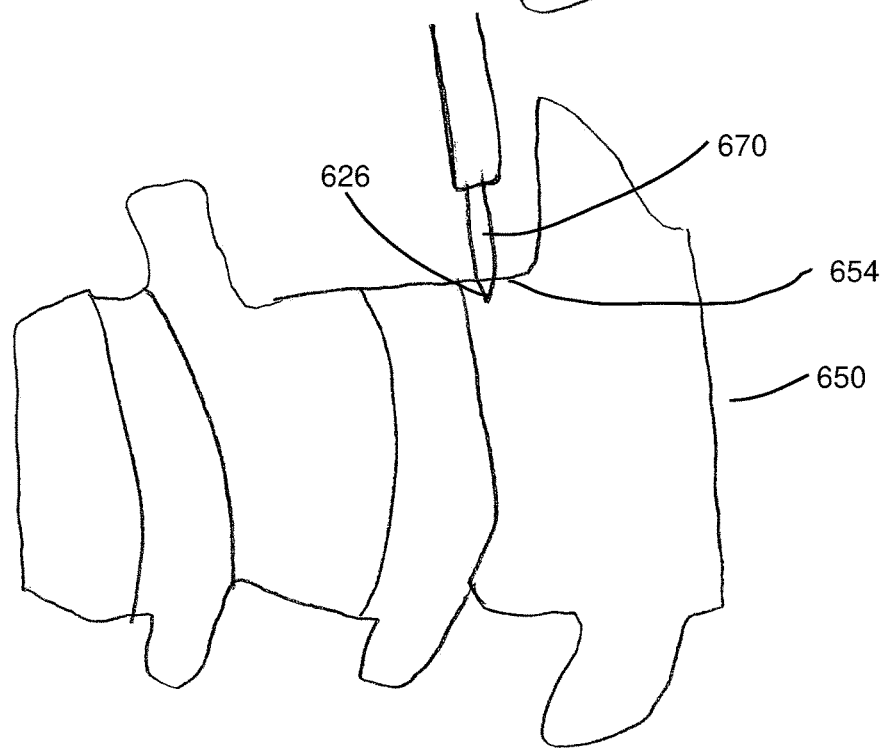
FIG. 39 illustrates an anterior view of a spine with an anchoring pin embodiment mounted lateral thereon consistent with at least one embodiment of the present disclosure.

In some embodiments the surgical retractor system 700 may include a mounting system to mount the tool in place relative to an internal organ, such as a vertebrae 652 or spine 650 for spinal surgery. As shown in FIGS. 35-36, and 39, blade 100 may include a tubular port 600. Port 600 is preferably set along a side of a blade 100 preferably along the longitudinal axis 104. Port 600 preferably includes a proximal hole 602 set along a proximal end or base 121 of blade 100, set between ridge 106 and tab 105. Port 600 is preferably set along interior side 114 and extends the length or, or a majority of the length of, the blade 100. Anchoring pin 670 or shim 671 may be inserted through a proximal hole 602 through opening edge 606 and pass through interior of port 600 to exit sital edge 610 and distal hole 604 along tip 101. In some embodiments an anchoring pin 620 may be used. Anchoring pin 620 includes shaft 622 set mostly though port 600. Beyond distal hole 604, anchoring pin 620 may include collar 624 to support a narrow point 626. Narrow point 626 of anchoring pin 620 is preferably used to set anchoring pin 620 into an endplate 654 of a vertebrae 652, preferably the superior endplate of the inferior vertebral body. In alternative embodiments, as demonstrated in FIGS. 35 and 37-38, a flat port 631 may be used to complement the shape of a flat shim 671. Shim 671 preferably includes an interior side 632 set against the interior side 114 of the blade 100, and an exterior side 634 facing the channel. As shown in FIG. 38 point 636 set along the distal end of shim 671 may be used to penetrate disc 656 in patient spine 650 to secure the relative location of the tool. When using the shim 671 embodiment grooves may be set along the interior side 141 of the blade 100 rather than a complete port 600. It is preferred that the port 600 is set along the longitudinal and rotating axis 104 of the blade 100 to ensure that the blade may freely rotate relative to the spine 650 (in tubular pin embodiments) while the blade assembly 150 is expanded 152 and contracted 151. When anchoring with the pin 670, or more importantly via shim 671 through the disc 656 or onto any internal organ, one may preferably monitor nerves via setting an electrode on the tip or exterior side of the blade to motor electrical activity from a remote portion of the patient's body, as is known in the art.

We claim:

1. A surgical retractor system comprising:
a plurality of blades, wherein each blade comprises an interior side, an exterior side, a distal end, and a proximal end, and wherein each blade defines a longitudinal axis;
wherein the exterior side of at least one of said plurality of blades is in contact with an interior edge of an adjacent one of said plurality of blades along the blade length from the proximal end to the distal end;
wherein the proximal end of each of said plurality of blades is coupled to a guide plate, said guide plate is rotatably coupled distally to a top plate; and
wherein each blade of said plurality of blades is in contact with an adjacent blade in both an open and a closed position.

2. The surgical retractor system of claim 1, wherein each of said plurality of blades proximal end is coupled to a pair of pins extending in a pin axis in a distal direction parallel to said longitudinal axis.

3. The surgical retractor system of claim 2, wherein each of said pairs of pins are coupled to said plurality of blades via a blade assembly holder.

4. The surgical retractor system of claim 3, wherein said blade assembly holder comprises a blade holder comprising a blade slot for receiving a portion of a blade of said plurality of blades, and a screw holder mated to said blade holder, said pair of pins extending distally from a pin aperture in said screw holder.

5. The surgical retractor system of claim 4, wherein said guide plate is circular and defines a plane perpendicular to the longitudinal axes of the blades.

6. The surgical retractor system of claim 3, wherein each of said pair of pins is set within a pair of tracking slots in said guide plate.

7. The surgical retractor system of claim 6, wherein said guide plate pair of tracking slots comprises interior and exterior slots predetermining paths and orientations of the proximal end of said blades.

8. A surgical retractor system comprising:
a plurality of blades, wherein each blade comprises an interior side, an exterior side, a distal end, and a proximal end, and wherein each blade defines a longitudinal axis;
wherein the exterior side of at least one of said plurality of blades is in contact with an interior edge of an adjacent one of said plurality of blades along the blade length from the proximal end to the distal end;
wherein the proximal end of each of said plurality of blades is coupled to a guide plate, said guide plate is rotatably coupled distally to a top plate; and wherein each of said blades is coupled to said guide plate by a pair of parallel pins set at least partially through an interior slot on the guide plate and an exterior slot on the guide plate.

9. The surgical retractor system of claim 8, wherein said top plate is circular and further comprises a plurality of slots radially emanating from a center of said top plate.

10. The surgical retractor system of claim 9, wherein each of said plurality of blades is coupled to at least one proximally extending pin coupled to said plurality of blades via a blade assembly holder.

11. The surgical retractor system of claim 10, wherein each of said at least one proximally extending pins is set within at least one of said radially emanating slots in said top plate.

12. The surgical retractor system of claim 11, wherein said pair of parallel pins extend in a pin axis in a distal direction parallel to said longitudinal axis of a blade of said plurality of blades; and wherein said at least one proximally extending pin comprises a head and shoulder extending beyond the top plate and having a diameter greater than the at least one slot.

13. The surgical retractor system of claim 12, wherein said blade assembly holder comprises a blade holder comprising a blade slot for receiving a portion of a blade of said plurality of blades, and a screw holder mated to said blade holder, said at least one proximally extending pin extending proximally from a pin aperture in said blade assembly holder.

14. The surgical retractor system of claim 13, wherein said top plate further comprises a partial spur gear.

15. A method for retracting tissues to allow access to portions of a patient internal body, said method comprising the steps of:
inserting a distal end of a plurality of coaxial blades through an incision in the patient's body into a cavity;

expanding the plurality of coaxial blades to define a channel set between said plurality of coaxial blades while at least at some time causing an exterior side of at least one of said plurality of coaxial blades to contact with an interior edge of an adjacent one of said plurality of coaxial blades from a proximal end to a distal end of the blade;

forming a surgical portal through the channel defined by the plurality of coaxial blades;

locking a relative orientation of the plurality of coaxial blades to retain a fixed diameter of the channel;

accessing a surgical site through a proximal end of the channel;

contracting the plurality of coaxial blades to reduce the diameter of the channel set between said plurality of coaxial blades while maintaining each of the blades in contact from a distal end to a proximal end to each of two adjacent blades; and withdrawing the plurality of coaxial blades from the patient's body.

16. The method of claim 15 whereby a base of each of the plurality of coaxial blades is coupled to a guide plate; and said step of accessing is accomplished via passing through a first aperture in the guide plate.

17. The method of claim 15 whereby a base of each of the plurality of coaxial blades is coupled to a guide plate; and whereby the step of expanding is accomplished by rotating a top plate relative the guide plate causing top pins coupled to ends of each of the blades to extend through radial slots in the top plate and a pair of guide pins extending opposing the top pins and moving along a pair of angled slots in the guide plate.

18. The method of claim 17 whereby said step of expanding is accomplished via rotating a pinion mounted on a handle coupled with the guide plate, the pinion coupled to at least one tooth on the top plate, whereby rotating the pinion causes the top plate to rotate relative to the guide plate.

19. The method of claim 17 whereby said step of expanding is accomplished via rotating a handle fixedly coupled to the top plate relative a second handle fixedly coupled to the guide plate.

20. A surgical retractor system comprising:
a plurality of blades, wherein each blade comprises an interior side, an exterior side, a distal end, and a proximal end, and wherein each blade defines a longitudinal axis;
wherein the exterior side of at least one of said plurality of blades is in contact with an interior edge of an adjacent one of said plurality of blades along the blade length from the proximal end to the distal end;
wherein the proximal end of each of said plurality of blades is coupled to a guide plate, said guide plate is rotatably coupled distally to a top plate; wherein each of said plurality of blades proximal end is coupled to a pair of pins extending in a pin axis in a distal direction parallel to said longitudinal axis; wherein each of said pairs of pins is coupled to said plurality of blades via a blade assembly holder; and wherein said blade assembly holder comprises a blade holder comprising a blade slot for receiving a portion of a blade of said plurality of blades, and a screw holder mated to said blade holder, said pair of pins extending distally from a pin aperture in said screw holder.

* * * * *